US012595240B2

(12) United States Patent      (10) Patent No.:   US 12,595,240 B2

Lockemeyer et al.      (45) Date of Patent:     Apr. 7, 2026

(54) PROCESS FOR THE PRODUCTION OF ETHYLENE OXIDE

(71) Applicant: SHELL OIL COMPANY, Houston, TX (US)

(72) Inventors: John Robert Lockemeyer, Houston, TX (US); Randall Clayton Yeates, Houston, TX (US)

(73) Assignee: SHELL USA, INC., Houston, TX (US)

( * ) Notice: Subject to any disclaimer, the term of this patent is extended or adjusted under 35 U.S.C. 154(b) by 404 days.

(21) Appl. No.: 18/254,620

(22) PCT Filed: Jan. 7, 2022

(86) PCT No.: PCT/IB2022/050112

§ 371 (c)(1),
(2) Date: May 26, 2023

(87) PCT Pub. No.: WO2022/144866

PCT Pub. Date: Jul. 7, 2022

(65) Prior Publication Data

US 2024/0025869 A1     Jan. 25, 2024

(30) Foreign Application Priority Data

Dec. 29, 2020    (EP) .................................... 20217699

(51) Int. Cl.
   *C07D 301/03*       (2006.01)
   *B01J 21/04*       (2006.01)
             (Continued)

(52) U.S. Cl.
   CPC ............ *C07D 301/03* (2013.01); *B01J 21/04* (2013.01); *B01J 23/688* (2013.01); *B01J 35/19* (2024.01); *B01J 35/612* (2024.01)

(58) Field of Classification Search
   CPC ...... C07D 301/03; C07D 301/10; B01J 21/04; B01J 23/688; B01J 35/19; B01J 35/612
                (Continued)

(56) References Cited

U.S. PATENT DOCUMENTS

| 3,950,507 A | 4/1976 | Kuklina et al. |
| 4,379,134 A | 4/1983 | Weber et al. |

(Continued)

FOREIGN PATENT DOCUMENTS

| EP | 0352850 A1 | 1/1990 |
| WO | 03044002 A1 | 5/2003 |
| WO | 03044003 A1 | 5/2003 |

OTHER PUBLICATIONS

International Search Report and Written Opinion Received for PCT Patent Application No. PCT/IB2022/050112, Mailed on Mar. 14, 2022, 8 Pages.

(Continued)

*Primary Examiner* — Taylor V Oh
(74) *Attorney, Agent, or Firm* — SHELL USA, INC.

(57)            ABSTRACT

An ethylene oxide (EO) production process for the epoxidation of ethylene comprising:
   contacting an inlet feed gas with a catalyst having a fluoride-mineralized alpha-alumina carrier, silver, a rhenium promoter, and one or more alkali metal promoters.
At a cumulative EO production $cumEO_1$ of at least 0.2 kton $EO/m^3$ catalyst, the process is operating at a reaction temperature $T_1$ and with the inlet feed gas having an optimum overall catalyst chloriding effectiveness value $Cl_{eff_1}$ to produce EO with an EO production parameter value $EO_1$; and
   the process is subsequently operated such that at a cumulative EO production $cumEO_X$, $cumEO_X$ is at least 0.6 kton $EO/m^3$ catalyst greater than $cumEO_1$, the reaction temperature has an increased value $T_X$ to maintain EO (Continued)

production parameter $EO_1$ whilst the optimum overall catalyst chloriding effectiveness value of the inlet feed gas $Cl_{eff_X}$ is controlled such that the ratio of $Cl_{eff_X}/Cl_{eff_1}$ is from 0.8 to 1.2.

19 Claims, 8 Drawing Sheets

(51) Int. Cl.
 *B01J 23/68*   (2006.01)
 *B01J 35/00*   (2006.01)
 *B01J 35/61*   (2024.01)

(58) Field of Classification Search
 USPC .......................................................... 549/523
 See application file for complete search history.

(56) References Cited

U.S. PATENT DOCUMENTS

| | | | |
|---|---|---|---|
| 4,761,394 A | 8/1988 | Lauritzen | |
| 4,766,105 A | 8/1988 | Lauritzen | |
| 4,845,296 A | 7/1989 | Ahmed et al. | |
| 4,994,588 A | 2/1991 | Kapicak et al. | |
| 4,994,589 A | 2/1991 | Notermann | |
| 5,100,859 A | 3/1992 | Gerdes et al. | |
| 5,145,824 A | 9/1992 | Buffum et al. | |
| 5,380,697 A | 1/1995 | Matusz et al. | |
| 5,384,302 A | 1/1995 | Gerdes et al. | |
| 5,512,530 A | 4/1996 | Gerdes et al. | |
| 5,733,842 A | 3/1998 | Gerdes et al. | |
| 5,739,075 A | 4/1998 | Matusz | |
| 6,040,467 A | 3/2000 | Papavassiliou et al. | |
| 6,203,773 B1 | 3/2001 | Easley et al. | |
| 6,368,998 B1 | 4/2002 | Lockemeyer | |
| 6,656,874 B2 | 12/2003 | Lockemeyer | |
| 7,232,918 B2 | 6/2007 | Lockemeyer | |
| 7,560,411 B2 | 7/2009 | Yeates et al. | |
| 8,084,390 B2 | 12/2011 | Gerdes et al. | |
| 8,362,284 B2 | 1/2013 | Zhang et al. | |
| 8,389,751 B2 | 3/2013 | Zhang et al. | |
| 8,513,156 B2 | 8/2013 | Serafin et al. | |
| 8,536,083 B2 | 9/2013 | Yeates et al. | |
| 9,221,776 B2 | 12/2015 | Schmitz et al. | |
| 2012/0108832 A1 | 5/2012 | Chen et al. | |
| 2012/0171407 A1 | 7/2012 | Richard et al. | |
| 2018/0161761 A1 | 6/2018 | Yeates et al. | |

OTHER PUBLICATIONS

Shaklee et al., "Growth of α-Al2O3 Platelets in the HF-γ-Al2O3 System", Journal of the American Ceramic Society, Nov. 1994, vol. 77, Issue No. 11, pp. 2977-2984.

Daimon et al., "Morphology of corundum crystallized by heating mixture of ≠-Al2O3 and AlF3", Journal of Crystal Growth, 1986, vol. 75, pp. 348-352.

Kirk-Othmer, Encyclopedia of Chemical Technology, 3rd Edition, 1980, vol. 9, pp. 445-447.

Brunauer et al., "Adsorption of Gases in Multimolecular Layers", Journal of the American Chemical Society, Feb. 1938, vol. 60, pp. 309-319.

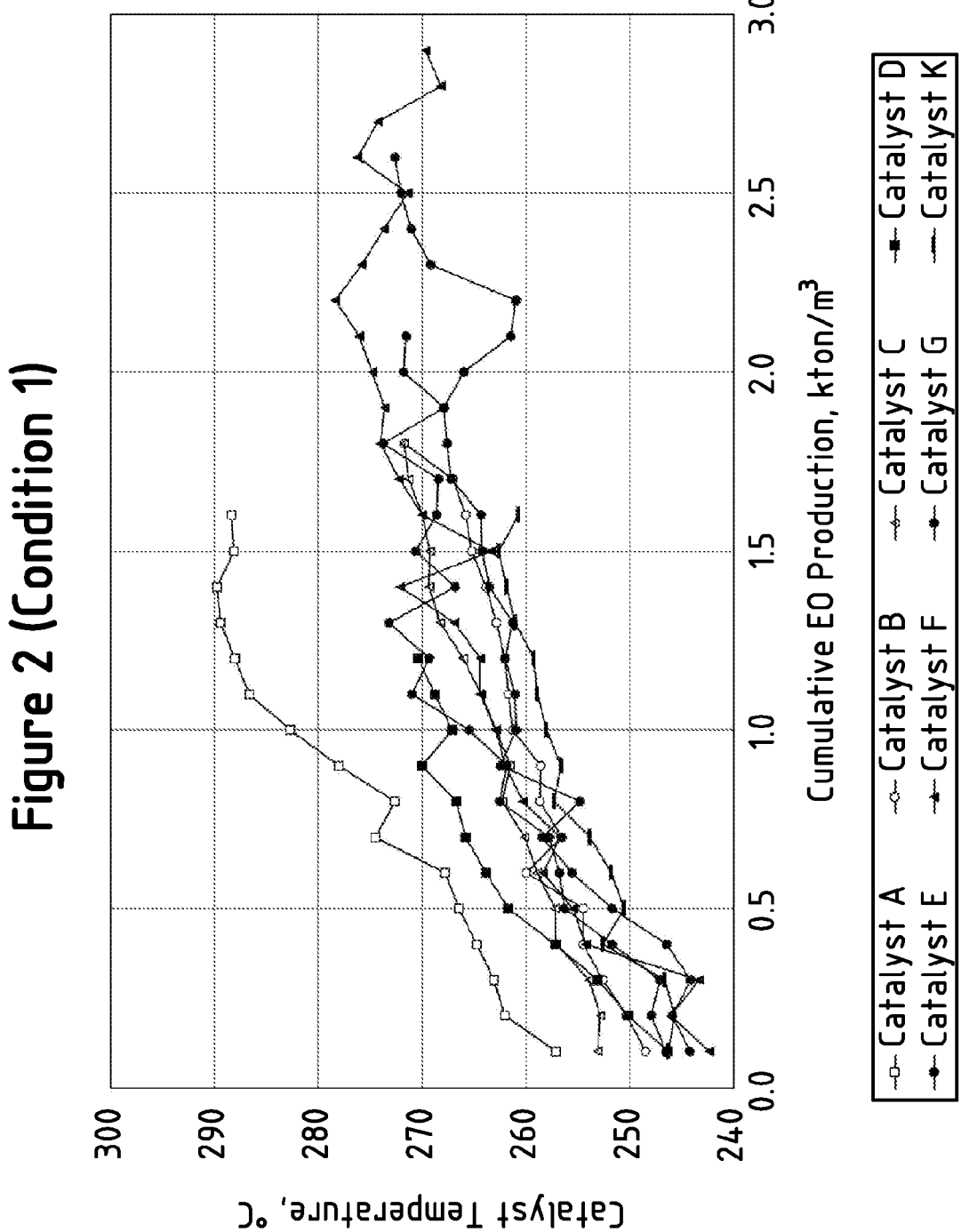
Figure 2 (Condition 1)

Figure 3 (Condition 1)
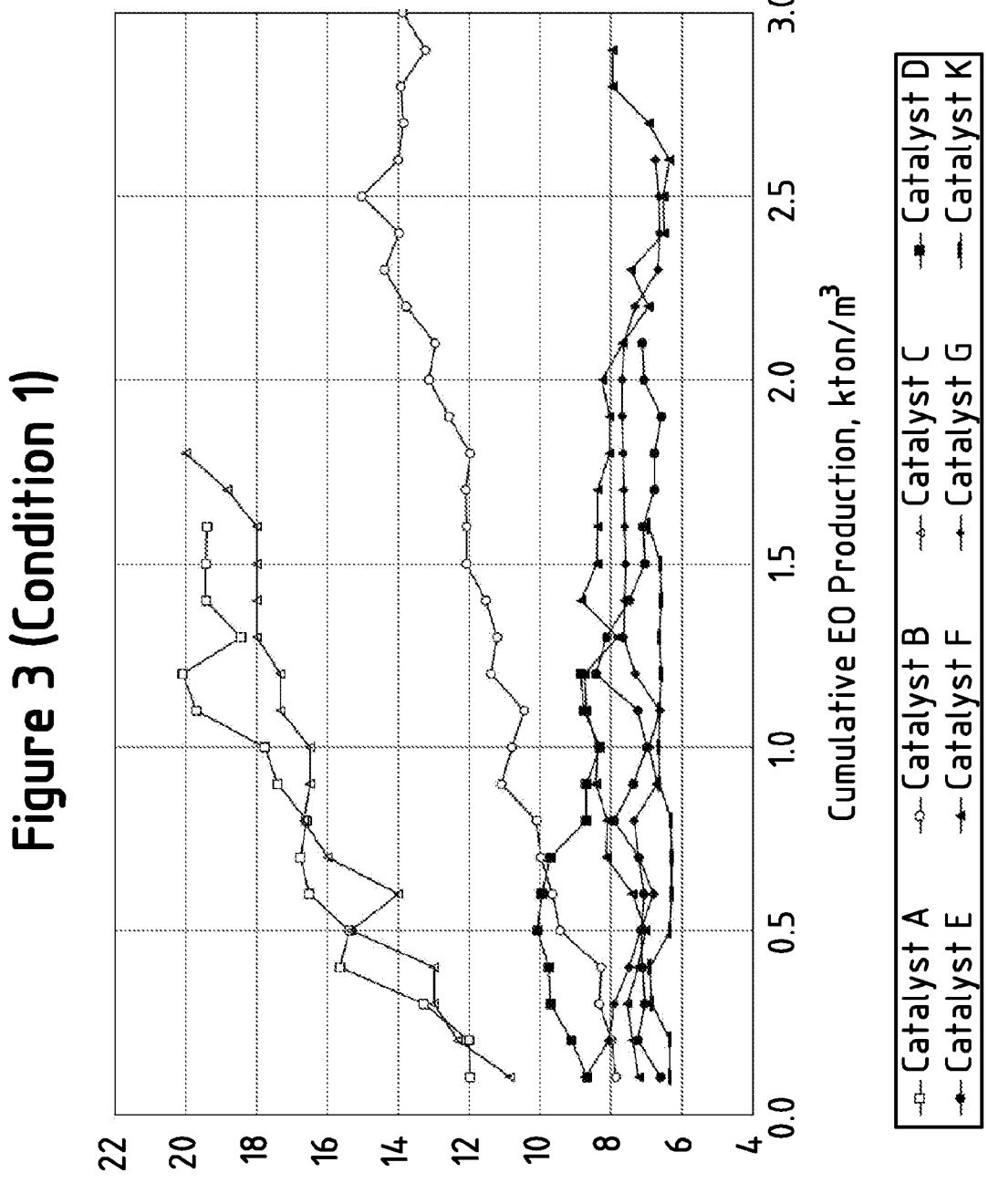

Figure 4 (Condition 1)
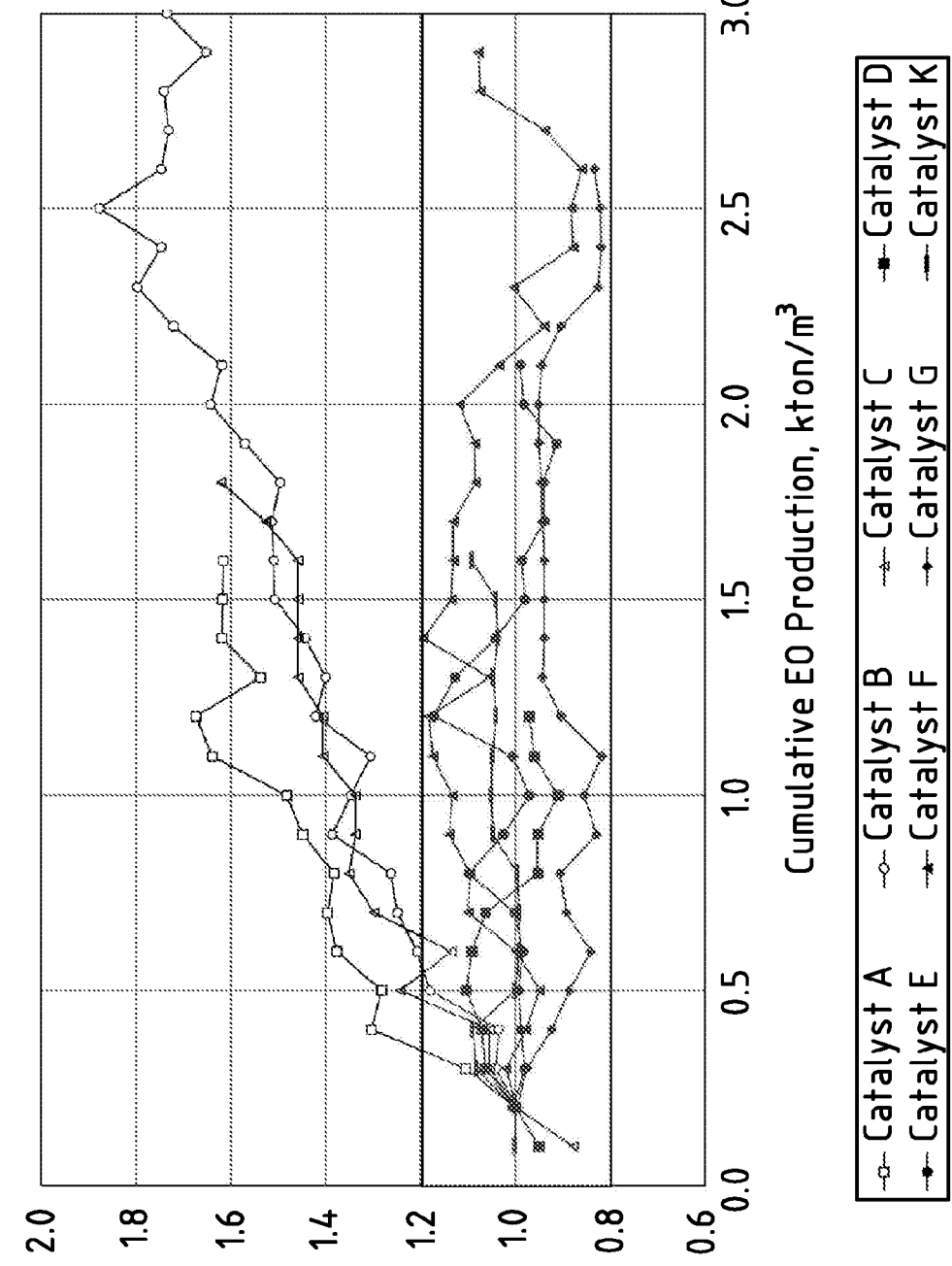

Figure 5 (Condition 2)
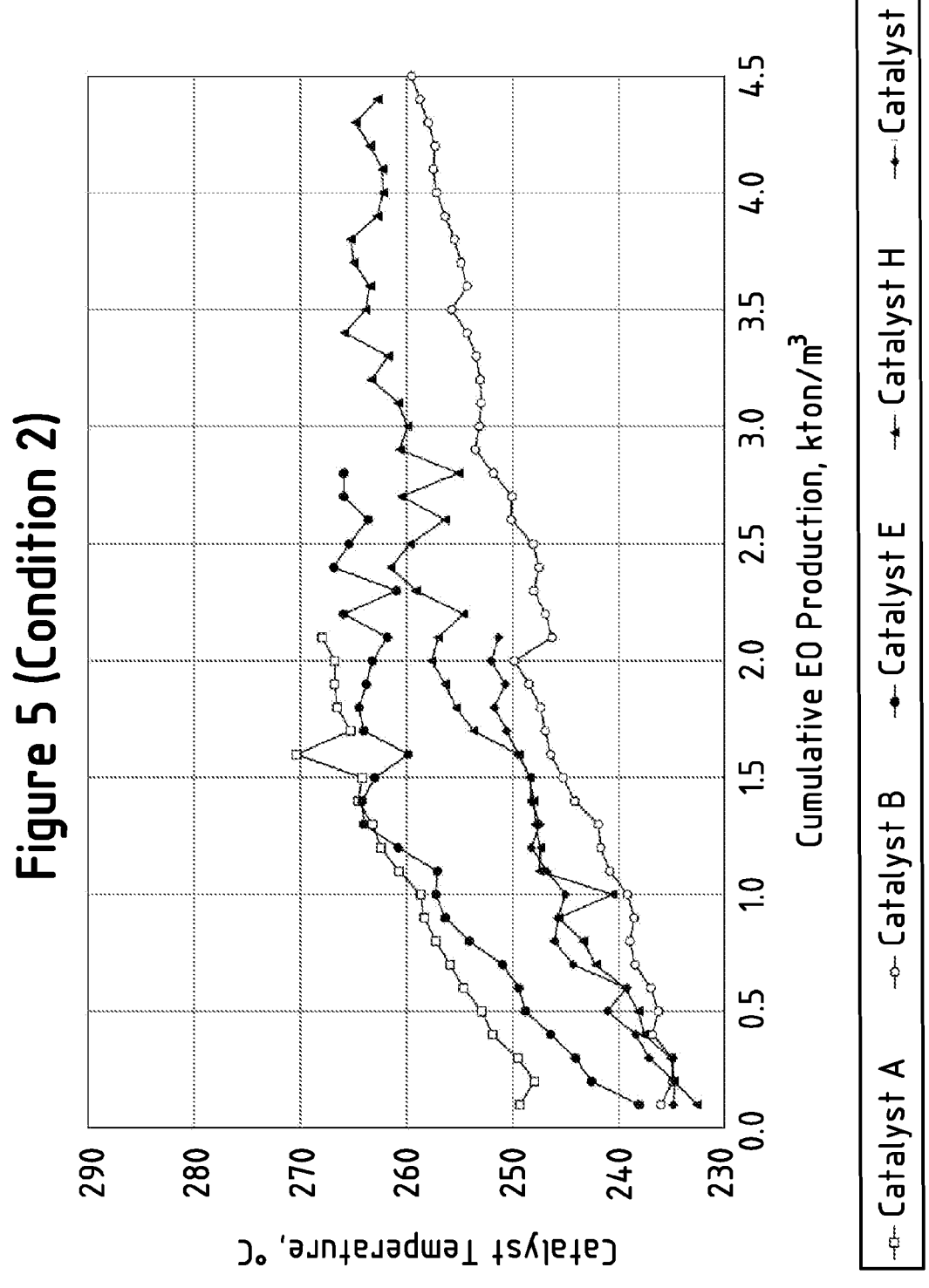
Cumulative EO Production, kton/m³
Catalyst Temperature, °C
Catalyst A   ⊡ Catalyst B   ⊸ Catalyst E   ● Catalyst H   ⊸ Catalyst I

Figure 6 (Condition 2)
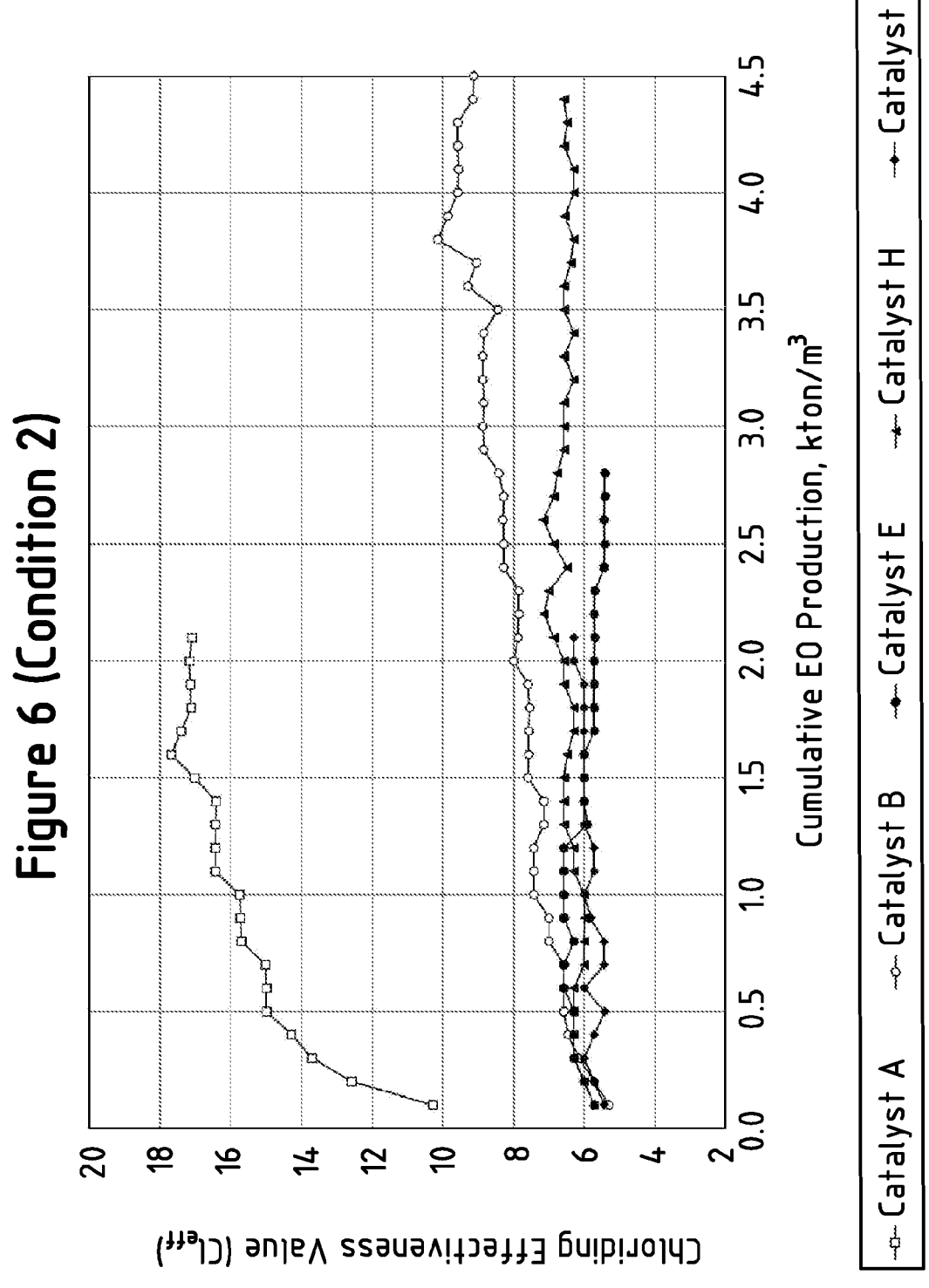
Cumulative EO Production, kton/m³
Chloriding Effectiveness Value (Cl$_{eff}$)
| —□— Catalyst A | —○— Catalyst B | —◆— Catalyst E | —▲— Catalyst H | —◆— Catalyst I |

Figure 7 (Condition 2)
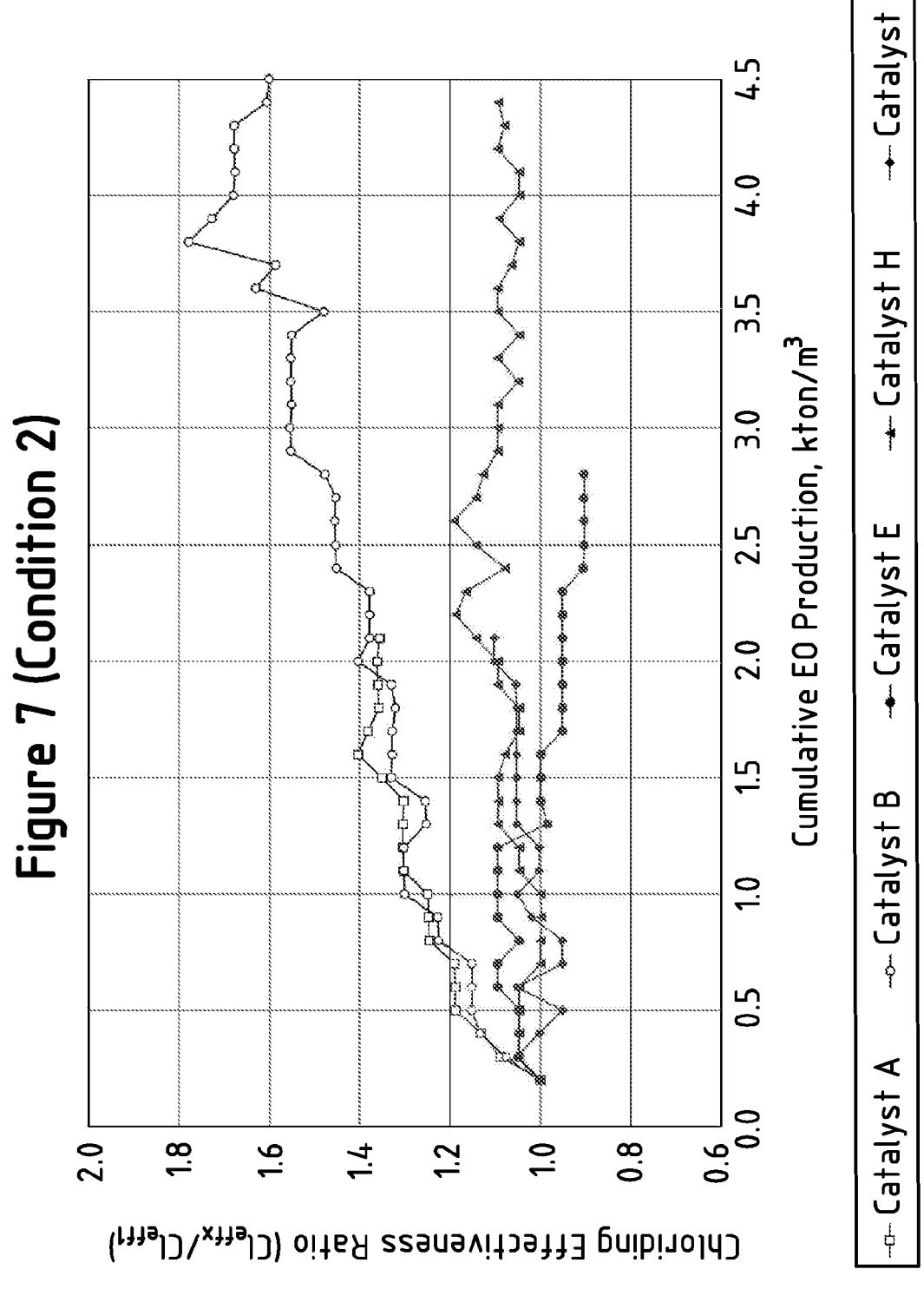
Cumulative EO Production, kton/m³
Chloriding Effectiveness Ratio ($Cl_{effx}/Cl_{eff1}$)
Catalyst A     Catalyst B     Catalyst E     Catalyst H     Catalyst I

Figure 8 (Condition 1)
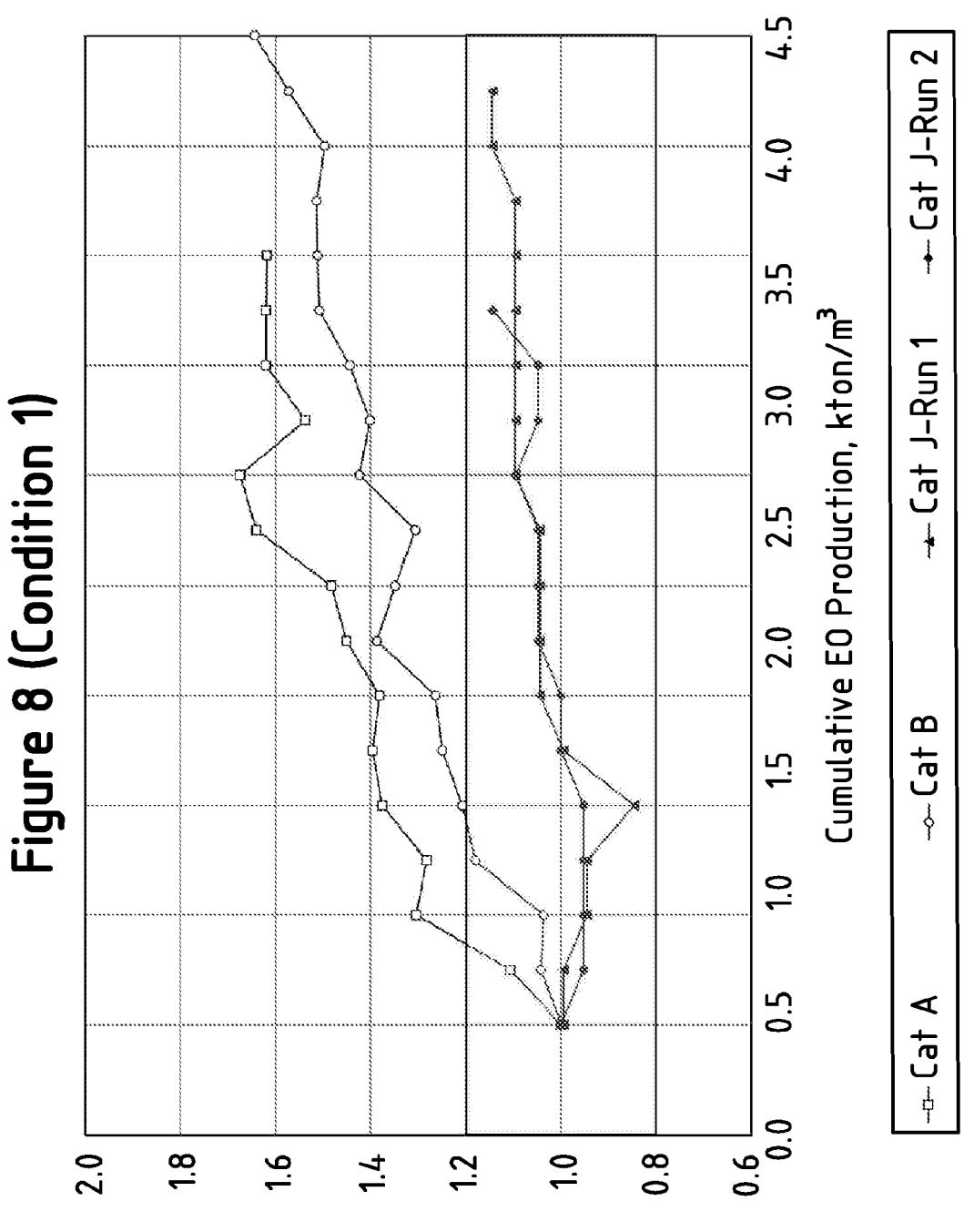

PROCESS FOR THE PRODUCTION OF ETHYLENE OXIDE

CROSS REFERENCE TO RELATED APPLICATIONS

This is a National stage application of International Application No. PCT/IB2022/050112, filed 7 Jan. 2022, which claims priority of European Application No. 20217699.6, filed 29 Dec. 2020 which is incorporated herein by reference in its entirety.

The present invention relates to a process for the production of ethylene oxide.

BACKGROUND OF THE INVENTION

Ethylene oxide (EO) is a valuable raw material that is well-known for its use as a versatile chemical intermediate in the production of a wide variety of chemicals and products. For example, ethylene oxide is often used to produce ethylene glycol, which is used in many diverse applications and may be found in a variety of products, including automotive engine antifreeze, hydraulic brake fluids, resins, fibers, solvents, paints, plastics, films, household and industrial cleaners, pharmaceutical preparations, and personal care items, such as cosmetics, shampoos, etc.

In the commercial production of ethylene oxide, ethylene is reacted with oxygen in the presence of an epoxidation catalyst, within an epoxidation reactor, to produce a gaseous stream at the outlet of the epoxidation reactor that comprises ethylene oxide. The reactor outlet stream typically comprises, in addition to ethylene oxide, unreacted ethylene, unreacted oxygen, a reaction modifier (e.g., organic chlorides), a dilution gas (e.g., nitrogen, methane or a combination thereof), various by-products of the epoxidation reaction (e.g., carbon dioxide and water) and various impurities (e.g., aldehydes, acidic impurities, argon, ethane, etc.).

In a next stage, the ethylene oxide is recovered from the reactor outlet stream, typically by supplying the reactor outlet stream to an ethylene oxide separation system, where the produced ethylene oxide is separated from the majority of the other gaseous constituents through contact with a recirculating solvent (commonly referred to as "lean absorbent").

The produced ethylene oxide is often further reacted, for example to provide glycols (e.g., ethylene glycol, diethylene glycol, triethylene glycol, etc.) via catalytic or non-catalytic hydrolysis. Typically, a majority of the remaining gaseous constituents in the ethylene oxide separation system (e.g., unreacted ethylene, unreacted oxygen, reaction modifier, dilution gas, etc.) are removed therefrom as an overhead gas stream, at least a portion of which is typically recycled to the epoxidation reactor via a recycle gas loop so as to minimize waste and/or increase savings, as the use of a recycle gas stream decreases the amount of fresh "make-up" feed (e.g., ethylene, oxygen, etc.) that needs to be supplied to the epoxidation reactor. Optionally, at least a portion of the recycle gas stream may be supplied to one or more separation and/or purification systems, such as a carbon dioxide separation system, etc., before it is supplied to the epoxidation reactor.

Ethylene oxide is formed by reacting ethylene with oxygen in the presence of a silver-based ethylene epoxidation catalyst. The catalyst performance may be assessed on the basis of selectivity, activity and stability of operation. The selectivity of an ethylene epoxidation catalyst, also known as the "efficiency", refers to the ability of the epoxidation catalyst to convert ethylene to the desired reaction product, ethylene oxide, versus the competing by-products (e.g., $CO_2$ and $H_2O$), and is typically expressed as the percentage of the number of moles of ethylene oxide produced per number of moles of ethylene reacted. Stability refers to how the selectivity and/or activity of the process changes during the time a charge of catalyst is being used, i.e., as more ethylene oxide is produced.

Various approaches to improving the performance of ethylene epoxidation catalysts, including improvements in selectivity, activity, and stability, have been investigated. For example, modern "high selectivity" silver-based epoxidation catalysts may comprise, in addition to silver, a rhenium promoter, and optionally one or more additional promoters, such as alkali metals (e.g., cesium, lithium, etc.), alkaline earth metals (e.g., magnesium), transition metals (e.g., tungsten), and main group non-metals (e.g., sulfur), are disclosed, for example, in U.S. Pat. Nos. 4,761,394 A and 4,766,105 A.

The selectivity determines to a large extent the economical attractiveness of an epoxidation process. For example, one percent improvement in the selectivity of the epoxidation process can substantially reduce the yearly operating costs of a large scale ethylene oxide plant. Further, the longer the activity and selectivity can be maintained at acceptable values, the longer the catalyst charge can be kept in the reactor and the more product is obtained. Quite modest improvements in the selectivity, activity, and maintenance of the selectivity and activity over long periods yield substantial dividends in terms of process efficiency.

Besides improvements in catalyst formulation, reaction modifiers have been found which may be added to the feed to improve the selectivity (cf. for example EP 0352850 A1). Such reaction modifiers suppress the undesirable oxidation of ethylene or ethylene oxide to carbon dioxide and water, relative to the desired formation of ethylene oxide, by a so-far unexplained mechanism. Suitable reaction modifiers are for example organic halides.

EP 0352850 A1 discloses that the high selectivity silver catalysts comprising rhenium tend to exhibit relatively steep selectivity curves for the modifier, viz. for high selectivity silver catalysts comprising rhenium, the selectivity varies considerably with relatively small changes in the quantity of the reaction modifier, and the selectivity exhibits a pronounced maximum, i.e. an optimum, at a certain quantity of the reaction modifier. This has been illustrated in EP 0352850 A1 (cf. FIG. 3 therein).

It is also well known in the field of ethylene epoxidation that when using a high selectivity silver epoxidation catalyst, i.e. a catalyst comprising silver, a rhenium promoter and optionally one or more additional promoters on a solid refractory support, as the catalyst ages thereby reducing catalyst activity, it is necessary to increase reaction temperature over time in order to maintain ethylene oxide production at the required level.

Moreover, the selectivity curves and more in particular the quantity of the reaction modifier where the selectivity is at maximum tend to change with the reaction temperature and, thus, during the catalyst life.

Consequently, when employing such high selectivity silver epoxidation catalysts in combination with a reaction modifier, the selectivity may vary to an undesirably large extent with changes of the reaction temperature and over the lifetime of the catalyst. Namely, when the reaction temperature is changed, for example to compensate for a reduction in the activity of the catalyst, it is necessary to maintain reaction conditions which are optimal with respect to maximizing the selectivity towards the ethylene oxide production.

Since the development of modern silver-based ethylene epoxidation catalysts in U.S. Pat. Nos. 4,761,394 A and 4,766,105 A, there has been continued teaching in the field over the last 30 years (for example, in EP 0352850 A1, WO 03/044003 A1, WO 2010/123844 A1, WO 2010/123842 A1 and WO 2015/100209 A1) that when using such high selectivity silver epoxidation catalysts, it is also necessary to increase the concentration of reaction modifier, in particular organic chlorides, in the feed gas over time as the catalyst ages to maintain maximum selectivity performance.

Thus, when applying a reaction modifier, the general teaching was that concentration of the reaction modifier in the feed should be chosen such that the selectivity is maintained at the maximum value. As a result, in the past, the optimum reaction modifier concentration at which the selectivity is at maximum was often found during the operation of the epoxidation process by a trial-and-error procedure, viz. by stepwise changing the reaction modifier supply rate and monitoring the effect on the selectivity. Such a procedure, however, was cumbersome, and would keep the process operating for some time at conditions which are less than the most economical. Moreover, the trial-and-error procedure would need to be redone when the feed composition changed, in order to adjust the concentration of the reaction modifier to the new reaction conditions.

However, in view of the accepted general teaching that when operating such catalysts, the optimum chloride reaction modifier concentration changes with temperature, various alternative methodologies and mathematical relationships have been described in the art in order to more efficiently determine the optimum chloride reaction modifier concentration at a given temperature and to adjust the feed gas accordingly without having to rely upon cumbersome trial-and-error procedures.

Said methods in the art usually focused on determination of the overall chloride reaction modifier concentration (M in WO 2015/100209 A1) or determination of the overall catalyst chloriding effectiveness value (Q or Z* in WO 03/044003 A1, WO 2010/123844 A1 and WO 2010/123842 A1), based on the slate of organic chlorides and hydrocarbons present in the feed gas.

As the optimum chloride concentration in a feed gas moves to higher concentrations over time with the associated increases in reaction temperature due to catalyst aging, it will be appreciated that the effective teaching of the prior art is that the value of the overall catalyst chloriding effectiveness will also increase over time when using an epoxidation catalyst comprising silver, rhenium and one or more alkali metal promoters on a solid refractory support.

The prior art acknowledges that continual determination of optimum chloride concentration (whether by trial-and-error methods or by calculation) and adjustment of chloride reaction modifier concentrations during operation of an industrial ethylene epoxidation process is difficult and cumbersome.

Furthermore, as an epoxidation catalyst comprising silver, rhenium and one or more alkali metal promoters ages and the optimum chloride concentration moves to higher concentrations, there is a greater demand placed on downstream purification equipment to manage the increased chloride content in the reactor system. That is to say, as chloride concentrations in the feed gas are increased over time, the downstream purification equipment will encounter increasing amounts of by-product organic chlorides, as well as acidic compounds. Such acidic compounds require the addition of alkaline compounds such as sodium hydroxide in order to maintain a reasonable pH in the aqueous part of the reactor system.

Thus, notwithstanding the improvements already achieved in the field of ethylene epoxidation, there is a desire to further improve the performance of ethylene epoxidation catalysts. In particular, it is highly desirable to find simplified methods for operating industrial ethylene epoxidation processes with the required level of production of ethylene oxide, which processes not only avoid the need to continually monitor and optimise chloride reaction modifier concentrations during operation, but which also avoid the need for increasing concentrations of chloride reaction modifier or the overall catalyst chloriding effectiveness value in a given feed gas over time as the epoxidation catalyst ages.

In the present invention, it has been surprisingly found that there exists specific epoxidation catalysts comprising silver, rhenium and one or more alkali metal promoters that do not require the chloride concentration in the feed gas or the optimum overall catalyst chloriding effectiveness value to be increased in response to increases in reaction temperature as the catalyst ages in order to maintain maximum selectivity performance at the required ethylene oxide production level.

SUMMARY OF THE INVENTION

The present invention provides a process for the epoxidation of ethylene comprising:

contacting an inlet feed gas comprising ethylene, oxygen and one or more reaction modifiers consisting of organic chlorides with an epoxidation catalyst comprising a carrier, and having silver, a rhenium promoter, and one or more alkali metal promoters deposited thereon; wherein the inlet feed gas has an overall catalyst chloriding effectiveness value ($Cl_{eff}$) represented by the formula:—

$$Cl_{eff} = \frac{(0.1 * [MC] + [EC] + 2 * [EDC] + [VC])}{(0.002 * [CH_4] + [C_2H_6] + 0.01 * [C_2H_4])} \tag{I}$$

wherein [MC], [EC], [EDC], and [VC] are the concentrations in ppmv of methyl chloride (MC), ethyl chloride (EC), ethylene dichloride (EDC), and vinyl chloride (VC), respectively, and [$CH_4$], [$C_2H_6$] and [$C_2H_4$] are the concentrations in mole percent of methane, ethane, and ethylene, respectively, in the inlet feed gas;

wherein at a cumulative ethylene oxide production $cumEO_1$ of at least 0.2 ktonethylene oxide/$m^3$ catalyst, said process is operating at a reaction temperature having a value $T_1$ and with the inlet feed gas having an optimum overall catalyst chloriding effectiveness value of $Cl_{eff_1}$ to produce ethylene oxide with an ethylene oxide production parameter at a value $EO_1$; and characterised in that the carrier is a fluoride-mineralized alpha-alumina carrier and said process is subsequently operated such that at a cumulative ethylene oxide production $cumEO_x$, wherein $cumEO_x$ is at least 0.6 kton ethylene oxide/$m^3$ catalyst greater than $cumEO_1$, the reaction temperature has an increased value $T_x$ to maintain said ethylene oxide production parameter at a value $EO_1$ whilst the optimum overall catalyst chloriding effectiveness value of the inlet feed gas $Cl_{eff_x}$ is controlled such that the ratio of $Cl_{eff_x}/Cl_{eff_1}$ is in the range of from 0.8 to 1.2.

FIGURES

Some specific example embodiments of the disclosure may be understood by referring, in part, to the following description and the accompanying figures.

FIG. 2 is a graph showing the activity profile for Catalysts A to G tested at Condition 1.

FIG. 3 is a graph depicting the optimum overall chloriding effectiveness values $(Cl_{eff})$ for Catalysts A to G over the production period shown in FIG. 2.

FIG. 4 is a graph depicting the ratio of the optimum overall chloriding effectiveness value at any time $(Cl_{eff_x})$ to the optimum overall chloriding effectiveness value at 0.2 $kton/m^3$ cumulative ethylene oxide production $(Cl_{eff_1})$ for each of Catalysts A to G over the production period shown in FIG. 2.

FIG. 5 is a graph showing the activity profile for Catalysts A, B, E, H and I tested at Condition 2.

FIG. 6 is a graph depicting the optimum overall chloriding effectiveness values $(Cl_{eff})$ for Catalysts A, B, E, H and I over the production period shown in FIG. 5.

FIG. 7 is a graph depicting the ratio of the optimum overall chloriding effectiveness value at any time $(Cl_{eff_x})$ to the optimum overall chloriding effectiveness value at 0.2 $kton/m^3$ cumulative ethylene oxide production $(Cl_{eff_1})$ for each of Catalysts A, B, E, H and I over the production period shown in FIG. 5.

FIG. 8 is a graph depicting the ratio of the optimum overall chloriding effectiveness value at any time $(Cl_{eff_x})$ to the optimum overall chloriding effectiveness value at 0.2 $kton/m^3$ cumulative ethylene oxide production $(Cl_{eff_1})$ for Catalysts A and B as compared to multiple runs of Catalyst J over the production period shown therein.

Figure 1:
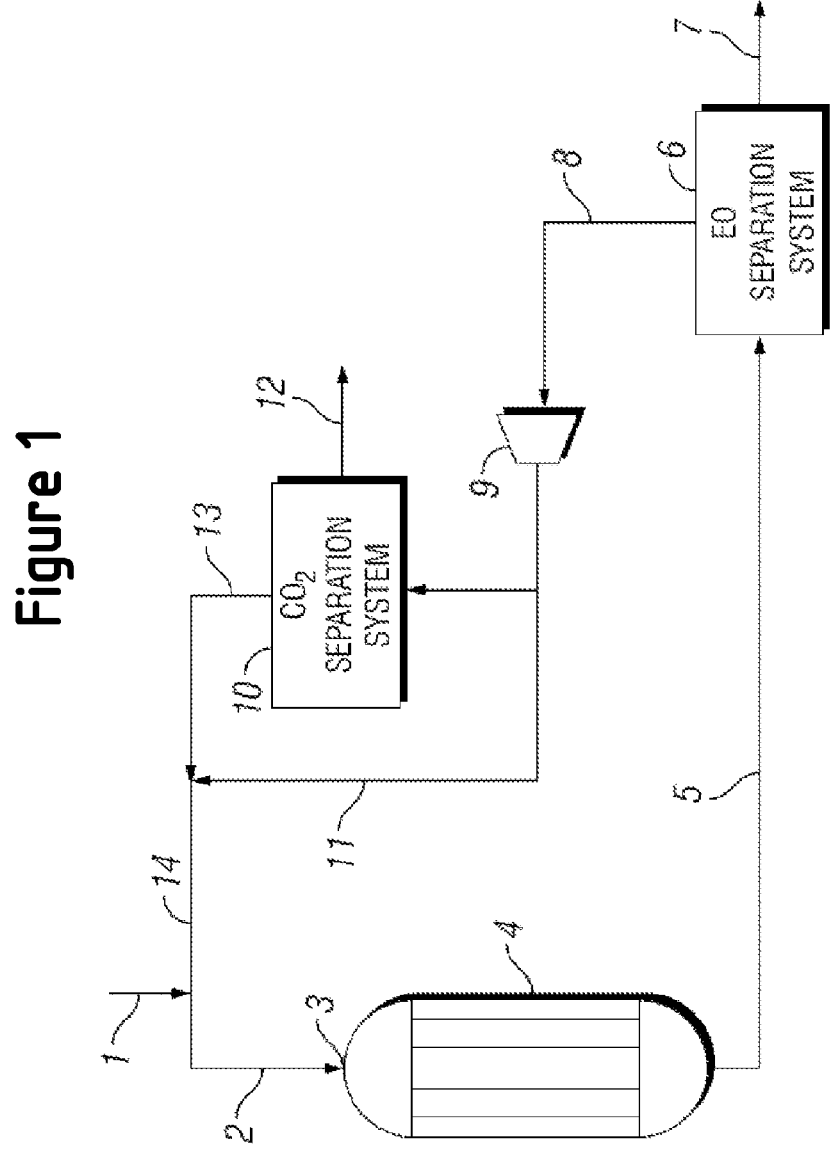
FIG. 1 is a schematic diagram showing an exemplary ethylene epoxidation process.

While the present disclosure is susceptible to various modifications and alternative forms, specific example embodiments have been shown in the figures and are herein described in more detail.

It should be understood, however, that the description of specific example embodiments is not intended to limit the invention to the particular forms disclosed, but on the contrary, this disclosure is to cover all modifications and equivalents as illustrated, in part, by the appended claims.

DETAILED DESCRIPTION OF THE INVENTION

To facilitate an understanding of the present disclosure, it is useful to define certain terms relating to the epoxidation reaction and epoxidation catalyst performance.

As used herein, "ethylene oxide production parameter" is a measure of the extent to which ethylene oxide is produced during a process for the epoxidation of ethylene. Said production parameter may be selected from the group consisting of product gas ethylene oxide concentration, ethylene oxide production rate and ethylene oxide production rate/ catalyst volume (also known as work rate (WR)).

The "activity" of an epoxidation catalyst is typically expressed in terms of the reaction temperature required to maintain a given ethylene oxide production parameter. In general, the activity of an epoxidation catalyst is a function of both the total number of catalytically active sites present on the surface of the epoxidation catalyst and the reaction rate of each site. Thus, the activity of a catalyst will decline (and, hence, the reaction temperature required to maintain the given ethylene oxide production parameter will increase) if either the number of catalytically active sites on the surface of an epoxidation catalyst is reduced and/or if the reaction rate for one or more of the active sites decreases (e.g., due to localized poisoning). The total number of active sites can be reduced in several ways, for example, by sintering of the catalytically active particles (i.e., silver particles), which results in an increase in silver particle size and correspondingly, a decrease in silver surface area. The number of active sites can also be reduced by reaction with chloride compounds in the inlet feed gas to form silver chloride compounds, in the presence of excess quantities of other unwanted elements, such as alkali metals or sulfur, which may enter the reactor as impurities or poisons and be deposited on the catalyst. Silver chloride compounds are inactive towards the epoxidation reaction. Further, the activity can decline due to catalyst poisoning, for example by exposure of the epoxidation catalyst to poisons, such as sulfur, iodine, silicon and phosphorus.

In many instances, the ethylene oxide production parameter is described in terms of "work rate", which refers to the amount of ethylene oxide produced in the epoxidation reactor per hour per unit volume of catalyst (e.g., kilograms or moles of ethylene oxide/hr/$m^3$ catalyst). As will be appreciated by those skilled in the art, an improvement in the activity of a catalyst, under a given set of conditions, is reflected by a lower reaction temperature required to maintain a given work rate at those conditions. Thus, an epoxidation catalyst having a "higher activity" in comparison to another epoxidation catalyst is one that, under a given set of conditions, employs a lower reaction temperature at a given work rate.

Alternatively, the "activity" of an epoxidation catalyst may be expressed as the mole percent of ethylene oxide contained in the reactor outlet stream relative to that in the inlet feed gas (the mole percent of ethylene oxide in the inlet feed gas typically, but not necessarily, approaches zero percent), while the reaction temperature is maintained substantially constant. Thus, in this instance, an epoxidation catalyst having a "higher activity" in comparison to another epoxidation catalyst is one that produces more ethylene oxide (i.e., has a higher work rate) at a given reaction temperature under the given set of conditions.

As used herein, the "selectivity" of an epoxidation catalyst, also known as "efficiency", refers to the ability of the epoxidation catalyst to convert ethylene to the desired reaction product, ethylene oxide, versus the competing by-products (e.g., $CO_2$ and $H_2O$), and is typically expressed as the percentage of the number of moles of ethylene oxide produced per number of moles of ethylene consumed in the reactor. As will be appreciated by one skilled in the art, an epoxidation catalyst having a "higher selectivity" in comparison to another epoxidation catalyst is one that, under a given set of conditions, provides for a greater number of moles of ethylene oxide produced per number of moles of ethylene consumed.

As used herein, "deactivation" refers to a permanent decrease or loss in catalytic activity and/or selectivity. During the epoxidation process, as the epoxidation catalyst is utilized, the catalyst eventually begins to "age" and its catalytic performance gradually deteriorates (e.g., the activity of the catalyst decreases due to, for example, silver sintering, etc.). Typically, the average useful lifespan of a modern epoxidation catalyst is approximately two to five years, depending upon factors such as the type of epoxidation catalyst, the reaction temperature, operating conditions, exposure to catalyst poisons, etc. Oftentimes, when catalytic activity begins to decline, the reaction temperature is increased in order to compensate and maintain a constant level of ethylene oxide production, as measured by the ethylene oxide production parameter (e.g., to maintain a desired work rate). However, this increase in reaction temperature often reduces catalyst selectivity and increases the rate of catalyst deactivation (i.e., accelerates the aging of the catalyst). The phenomenon of selectivity decline is complex and is dependent upon a number of factors, such as the catalyst activity, the operating conditions, the work rate, the catalyst age, the presence of poisons, etc. In general, the "stability" of an epoxidation catalyst is inversely proportional to the rate of catalyst deactivation and is correlative to the length of time that catalyst performance and productivity can be maintained at acceptable values before the catalyst needs to be exchanged for fresh catalyst. The term "stability" can be applied to both the activity decline and the selectivity decline over time. As will be readily appreciated, improvements in catalyst stability (either in activity stability and/or in selectivity stability) are highly desirable from an economic perspective because the epoxidation catalyst is a significant expense to a plant, as is the lost production that occurs due to plant shut down when the catalyst is exchanged.

As used herein, by the "end of catalyst life" is meant the catalyst has achieved its final cumulative EO production before it is removed from the reactor and, optionally, replaced with a fresh charge of catalyst. That is, a catalyst starts up and operates, producing EO during its operation. At some point later in time, that catalyst operation is stopped and the catalyst is removed from the reactor and replaced. The final cumulative EO production is the total amount of EO produced from start-up of the catalyst to its removal from the reactor. Normal catalyst life depends on many factors, as described hereinbelow. Typically, catalyst life is at least 1.5 kton/m³ cumulative EO production and may extend to 4.0 kton/m³ or more cumulative EO production. The decision on when to change out catalyst for a fresh charge may be dependent on a number of factors, including the prevailing catalyst activity, catalyst selectivity and productivity, turnaround schedules, statutory inspections, significant maintenance shutdowns, etc.

As discussed hereinbefore, the prior art teaches that as an epoxidation catalyst comprising silver, rhenium and one or more alkali metal promoters undergoes age-related activity decline, it is necessary to increase reaction temperature to maintain the ethylene oxide production parameter whilst also increasing the concentration of organic chloride reaction modifier in the feed gas to maintain maximum selectivity performance.

In the present invention, it has been surprisingly found that there exists specific epoxidation catalysts comprising silver, rhenium and one or more alkali metal promoters which do not require careful control of the concentration of organic chloride reaction modifier in the feed gas as the catalyst ages in order to maintain maximum selectivity performance.

The present invention therefore greatly simplifies industrial operation of ethylene epoxidation processes for the plant operator as maximum selectivity performance at a constant value of the ethylene oxide production parameter can be advantageously achieved by maintaining the concentration of organic chloride reaction modifier in the feed gas either constant or within a narrow concentration range for a given feed gas.

In circumstances wherein the feed gas undergoes minor variations in the concentrations of other feed gas components such as ethylene or hydrocarbons (for example, ethane), then under the present invention when using an epoxidation catalyst comprising a fluoride-mineralized alpha-alumina carrier, and having silver, a rhenium promoter and an alkali metal promoter deposited thereon, the EO plant operator will find operation greatly simplified as the EO plant operator no longer needs to conduct optimisation of chloride concentrations and may simply ensure the overall catalyst chloriding effectiveness value is maintained within a narrow range throughout catalyst operation.

Epoxidation Process

The epoxidation process of the present invention may be carried out in a variety of ways known in the art, however, it is preferred to carry out the epoxidation process as a continuous, gas-phase process. Similarly, the epoxidation process may be carried out in any known epoxidation reactor (e.g., any reactor vessel used to react ethylene and oxygen), such as a fixed bed reactor (e.g., a fixed bed tubular reactor), a continuous stirred tank reactor (CSTR), a fluid bed reactor, etc. Additionally, a plurality of epoxidation reactors may be used in parallel or series.

One commercial example of a suitable epoxidation reactor is a vertical shell-and-tube heat exchanger, wherein the shell contains a coolant (e.g., heat transfer fluid (such as tetralin), water, etc.) to regulate the temperature of the epoxidation reactor and wherein the plurality of tubes are substantially parallel, elongated tubes that contain the epoxidation catalyst. While the size and number of tubes may vary from reactor to reactor, a typical tube used in a commercial reactor may have a length of from 3 to 25 meters, from 5 to 20 meters, or from 6 to 15 meters. Similarly, the reactor tubes may have an internal tube diameter of from 5 to 80 millimeters, from 10 to 75 millimeters, or from 20 to 60 millimeters. The number of tubes present in an epoxidation reactor can vary widely and may range in the thousands, for example up to 22,000, or from 1,000 to 11,000, or from 1,500 to 18,500.

The portion of the epoxidation reactor containing the epoxidation catalyst (e.g., reactor tubes) is commonly referred to as the "catalyst bed". In general, the amount of epoxidation catalyst in the catalyst bed, the height of the catalyst bed and the packing density of the epoxidation catalyst within the catalyst bed (i.e., the "tube packing density") may vary over a wide range, depending upon, for example, the size and number of tubes present within the epoxidation reactor and the size and shape of the epoxidation catalyst. However, typical ranges for the tube packing density may be from 400 to 1500 kg/m³. Similarly, typical ranges for catalyst bed height may be from 50% to 100% of the reactor tube length. In those embodiments where the catalyst bed height is less than 100% of the reactor tube length, the remaining portion of the tube may be empty or optionally comprise particles of a non-catalytic or inert material.

FIG. 1 is a schematic representation showing an exemplary ethylene epoxidation process. Ethylene, oxygen, a dilution gas, and a reaction modifier are supplied at 1 to recycle gas stream 14 to define inlet feed gas 2, which is supplied to inlet 3 of epoxidation reactor 4. Within epoxidation reactor 4, ethylene and oxygen react in the presence of an epoxidation catalyst. Reactor outlet stream 5, which comprises ethylene oxide, unreacted ethylene, unreacted oxygen, reaction modifier, dilution gas, various by-products of the epoxidation reaction (e.g., carbon dioxide and water) and various impurities, is withdrawn from epoxidation reactor 4 and supplied to ethylene oxide separation system 6. At least a portion of net product stream 7 from ethylene oxide separation system 6 may be further reacted, for example to provide glycols (e.g., ethylene glycol, diethylene glycol, triethylene glycol, etc.) via catalytic or non-catalytic hydrolysis.

A majority of the gaseous constituents not absorbed in ethylene oxide separation system 6 (e.g., unreacted ethylene, unreacted oxygen, reaction modifier, dilution gas, etc.) are withdrawn therefrom as overhead gas stream 8 and supplied to recycle gas compressor 9. At least a portion of overhead gas stream 8 may then be supplied to carbon dioxide separation system 10, while the remaining portion (if any) bypasses the carbon dioxide separation system via bypass stream 11. In carbon dioxide separation system 10, carbon dioxide is removed and exits via carbon dioxide stream 12, while overhead gas stream 13 is combined with bypass stream 11 to form recycle gas stream 14. As previously mentioned, recycle gas stream 14 is combined with "make-up" ethylene, oxygen, dilution gas and reaction modifier to form inlet feed gas 2.

The epoxidation processes described herein are not limited to any particular reactor or flow configurations, and those depicted in FIG. 1 are merely exemplary. Additionally, the sequence in which various feed components are introduced into the process and their respective points of introduction, as well as the flow connections, may be varied from that depicted in FIG. 1.

Inlet Feed Gas Composition

In accordance with the epoxidation processes described herein, the inlet feed gas comprises ethylene, oxygen and one or more reaction modifiers consisting of organic chlorides. Optionally, the inlet feed gas may further comprise non-chloride containing hydrocarbons such as ethane, carbon dioxide, a dilution gas, water vapor, and combinations thereof.

As used herein, the term "inlet feed gas" is understood to refer to the totality of the gaseous stream at the inlet of the epoxidation reactor. Thus, as will be appreciated by one skilled in the art, the inlet feed gas is often comprised of a combination of one or more gaseous stream(s), such as an ethylene stream, an oxygen stream, a reaction modifier injection stream, a recycle gas stream, etc.

Ethylene may be present in the inlet feed gas in a concentration that may vary over a wide range. However, ethylene is typically present in the inlet feed gas in a concentration of at least 5 mole-%, relative to the total inlet feed gas, or at least 8 mole-%, or at least 10 mole-%, or at least 12 mole-%, or at least 14 mole-%, or at least 20 mole-%, or at least 25 mole-%, on the same basis. Similarly, ethylene is typically present in the inlet feed gas in a concentration of at most 65 mole-%, or at most 60 mole-%, or at most 55 mole-%, or at most 50 mole-%, or at most 48 mole-%, on the same basis. In some embodiments, ethylene may be present in the inlet feed gas in a concentration of from 5 mole-% to 60 mole-%, relative to the total inlet feed gas, or from 10 mole-% to 50 mole-%, or from 12 mole-% to 48 mole-%, on the same basis.

In addition to ethylene, the inlet feed gas further comprises oxygen, which may be provided either as pure oxygen or air. See "Kirk-Othmer Encyclopedia of Chemical Technology", 3rd edition, Volume 9, 1980, pp. 445-447. In an air-based process, air or air enriched with oxygen is employed, while in an oxygen-based process, high-purity (at least 95 mole-%) oxygen or very high purity (at least 99.5 mole-%) oxygen is employed. Reference may be made to U.S. Pat. No. 6,040,467 A, incorporated by reference herein, for further description of oxygen-based epoxidation processes. Presently, most epoxidation plants are oxygen-based, which is preferred. Typically, in oxygen-based processes, the inlet feed gas further comprises a dilution gas, which will be discussed in more detail below, to maintain the oxygen concentration below the maximum level allowed by flammability considerations.

In general, the oxygen concentration in the inlet feed gas should be less than the concentration of oxygen that would form a flammable mixture at either the reactor inlet or the reactor outlet at the prevailing operating conditions. Often, in practice, the oxygen concentration in the inlet feed gas may be no greater than a pre-defined percentage (e.g., 95%, 90%, etc.) of oxygen that would form a flammable mixture at either the epoxidation reactor inlet or the epoxidation reactor outlet at the prevailing operating conditions. Although the oxygen concentration may vary over a wide range, the oxygen concentration in the inlet feed gas is typically at least 0.5 mole-%, relative to the total inlet feed gas, or at least 1 mole-%, or at least 2 mole-%, or at least 3 mole-%, or at least 4 mole-%, or at least 5 mole-%, on the same basis. Similarly, the oxygen concentration of the inlet feed gas is typically at most 20 mole-%, relative to the total inlet feed gas, or at most 15 mole-%, or at most 12 mole-%, or at most 10 mole-%, on the same basis. In some embodiments, oxygen may be present in the inlet feed gas in a concentration of from 1 mole-% to 15 mole-%, relative to the total inlet feed gas, or from 2 mole-% to 12 mole-%, or from 3 mole-% to 10 mole-%, on the same basis. Typically, as the oxygen concentration in the inlet feed gas increases, the required operating temperature decreases. However as previously mentioned, in practice, flammability is generally the limiting factor for the maximum concentration of oxygen in the inlet feed gas. Accordingly, in order to remain outside the flammable regime, the oxygen concentration of the inlet feed gas may be lowered as the ethylene concentration of the inlet feed gas is increased. It is within the ability of one skilled in the art to determine a suitable concentration of oxygen to be included in the inlet feed gas, taking into consideration, for example, the overall inlet feed gas composition, along with the other operating conditions, such as pressure and temperature.

In addition to ethylene and oxygen, the inlet feed gas further comprises one or more reaction modifiers consisting of organic chlorides.

For the avoidance of doubt, the only reaction modifiers in the inlet feed gas used in the process of the present invention are organic chlorides. That is to say, the inlet feed gas is substantially free, and preferably completely free, of nitrogen-containing reaction modifiers. That is to say, the inlet feed gas may comprise less than 100 ppm of a nitrogen-containing reaction modifier, preferably less than 10 ppm, more preferably less than 1 ppm, and most preferably 0 ppm of a nitrogen-containing reaction modifier. As used herein, the term "nitrogen-containing reaction modifier" refers to a gaseous compound or volatile liquid that is present as, or capable of forming, nitrogen oxides in oxidizing conditions. Examples of nitrogen-containing reaction modifiers include, but are not limited to, NO, $NO_2$, $N_2O_3$, $N_2O_4$, $N_2O_5$ or any substance capable of forming one of the aforementioned gases under epoxidation conditions (e.g., hydrazine, hydroxylamine, ammonia, organic nitro compounds (such as nitromethane, nitroethane, nitrobenzene, etc.), amines, amides, organic nitrites (such as methyl nitrite), nitriles (such as acetonitrile)), and a combination thereof.

Examples of suitable organic chloride reaction modifiers that may be used in the inlet feed include, but are not limited to, C1 to C3 chlorohydrocarbons. Specific examples of suitable organic chlorides include, but are not limited to, methyl chloride, ethyl chloride, ethylene dichloride, vinyl chloride, and combinations thereof.

The one or more reaction modifiers are generally present in the inlet feed gas in a total concentration of 0.1 parts per million by volume (ppmv) or greater, relative to the total inlet feed gas, or 0.3 ppmv or greater, or 0.5 ppmv or greater, on the same basis. Similarly, the one or more reaction modifiers are generally present in the inlet feed gas in a total concentration of at most 25 ppmv, relative to the total inlet feed gas, or at most 22 ppmv, or at most 20 ppmv, on the same basis. In some embodiments, the one or more reaction modifiers may be present in the inlet feed gas in a total concentration of from 0.1 to 25 ppmv, relative to the total inlet feed gas, or from 0.3 to 20 ppmv, on the same basis.

As is discussed in WO 03/044002 A1, WO 03/044003 A1 and WO 2010/123844 A1, it is believed that the ability of organic chloride reaction modifiers to enhance the performance (e.g., selectivity and/or activity) of an epoxidation catalyst comprising silver, rhenium and one or more alkali metal promoters on a solid refractory support in the production of ethylene oxide depends on the extent to which said organic chlorides chlorinate the surface of the epoxidation catalyst, for example, by depositing particular chlorine species such as atomic chlorine or chloride ions on the catalyst. However, hydrocarbons lacking chlorine atoms that are present in the inlet feed gas are believed to strip chlorides from the surface of the catalyst, and therefore, detract from the overall performance enhancement provided by the organic chloride reaction modifiers.

Paraffinic compounds, such as ethane or methane, are believed to be especially effective at stripping chlorides from the epoxidation catalyst. However, ethylene is also believed to act to strip chlorides from the catalyst.

Some of these hydrocarbons may also be introduced as impurities in the ethylene feed or may be present for other reasons (such as the use of recycle stream 14). Typically, the preferred concentration of ethane in the inlet feed gas 2, when present, is from 0 to about 2 mole-%.

Given the competing effects of the organic chloride reaction modifiers and the chloride-removing hydrocarbons in inlet feed gas 2, it is convenient to define an "overall catalyst chloriding effectiveness value" that represents the net effect of organic chloride reaction modifiers in chloriding the epoxidation catalyst.

Said overall catalyst chloriding effectiveness value can be defined as the dimensionless quantity $Cl_{eff}$ and represented by the following formula:

$$Cl_{eff} = \frac{(0.1 * [MC] + [EC] + 2 * [EDC] + [VC])}{(0.002 * [CH_4] + [C_2H_6] + 0.01 * [C_2H_4])} \quad (I)$$

wherein MC, EC, EDC, and VC are the concentrations in ppmv of methyl chloride (MC), ethyl chloride (EC), ethylene dichloride (EDC), and vinyl chloride (VC), respectively, and $CH_4$, $C_2H_6$ and $C_2H_4$ are the concentrations in mole percent of methane, ethane, and ethylene, respectively, in the inlet feed gas.

Hence, if ethyl chloride is the only organic chloride reaction modifier present in inlet feed gas 2, then the numerator in equation (I) is the ethyl chloride concentration in ppmv as the concentrations of methyl chloride, ethylene dichloride and vinyl chloride will be zero and therefore not contribute to the numerator in equation (I). Similarly. if vinyl chloride, methyl chloride or ethylene dichloride are used alone or in conjunction with ethyl chloride in the inlet feed gas, then the numerator in equation (I) is adjusted accordingly with regard to the concentrations thereof in ppmv.

In embodiments wherein there are organic chlorides present in the inlet feed gas other than methyl chloride, ethyl chloride, ethylene dichloride and/or vinyl chloride, then for the purposes of calculating $Cl_{eff}$ using equation (I), the concentration of said organic chlorides are discounted. Similarly, if there are any additional hydrocarbons present in the inlet feed gas besides $CH_4$, $C_2H_6$ and $C_2H_4$, then for the purposes of calculating $Cl_{eff}$ using equation (I), the concentration of said additional hydrocarbons are discounted.

Although the organic chloride reaction modifier may be supplied as a single species, upon contact with the epoxidation catalyst, other species may be formed leading to a mixture of organic chloride reaction modifiers in the gas phase. Consequently, if the reaction gases are recycled, such as via recycle stream 14, a mixture of species will be found in the inlet of the reactor.

In particular, the recycled reaction gases at the inlet may contain ethyl chloride, vinyl chloride, ethylene dichloride and methyl chloride, even though only ethyl chloride or ethylene dichloride is supplied to the system. The concentrations of ethyl chloride, vinyl chloride, and ethylene dichloride must be considered in calculating $Cl_{eff}$.

In typical operation, the overall chloriding effectiveness value ($Cl_{eff}$) is adjusted to achieve the highest possible (maximum) selectivity at a particular set of operating conditions. Herein, when the overall chloriding effectiveness value has been selected to achieve maximum selectivity under a set of operating conditions, this is denoted as the "optimum overall chloriding effectiveness value".

As mentioned hereinbefore, the prior art (e.g. WO 03/044003 A1, WO 2010/123844 A1, WO 2010/123842 A1 and WO 2015/100209 A1) teaches that as an epoxidation catalyst comprising silver, rhenium and one or more alkali metal promoters ages over time during a process for the epoxidation of ethylene and the reaction temperature is increased to counter any losses in catalyst activity, the optimum chloride concentration for maximum selectivity performance also moves to higher concentrations.

However, in the present invention, it has been surprisingly found that the specific epoxidation catalysts described herein do not require significant changes in chloride concentration over time to maintain maximum selectivity performance at a constant value of the ethylene oxide production parameter as reaction temperature is increased due to catalyst ageing.

Accordingly, relative to an initial point in time during an epoxidation process wherein there is a cumulative ethylene oxide production $cumEO_1$ of at least 0.2 kton ethylene oxide/m$^3$ catalyst, preferably at least 0.25 kton ethylene oxide/m$^3$ catalyst and more preferably at least 0.3 kton ethylene oxide/m$^3$ catalyst, (and said process is operating at a reaction temperature having a value $T_1$ and with the inlet feed gas having an optimum overall catalyst chloriding effectiveness value of $Cl_{eff}$ to produce ethylene oxide with an ethylene oxide production parameter at a value $EO_1$), the present invention provides the EO plant operator with a convenient method for subsequent operation of said process as the epoxidation catalyst further ages over time.

Thus, in the present invention, as the reaction temperature is increased over time to a value $T_x$ to maintain said ethylene oxide production parameter at a value $EO_1$, the EO plant operator may conveniently maintain maximum catalyst selectivity by controlling the optimum overall catalyst chloriding effectiveness value of the inlet feed gas $Cl_{eff_x}$ such that the ratio of $Cl_{eff_x}/Cl_{eff_1}$ is in the range of from 0.8 to 1.2, preferably in the range of from 0.9 to 1.1.

In the present invention, by "maintain said ethylene oxide production parameter at a value $EO_1$" is meant that the ethylene oxide production parameter is substantially the same as $EO_1$. That is to say, said ethylene oxide production parameter is controlled at the target value of $EO_1$, which due to normal operational variation in commercial practice may fluctuate between ±5% of the target value, preferably ±3% of the target value, more preferably ±2% of the target value.

In a preferred embodiment of the present invention, at a cumulative ethylene oxide production $cumEO_x$, the reaction temperature $T_x$ is greater than $T_1$ by at least 3° C., preferably by at least 5° C. and most preferably by at least 10° C.

In another preferred embodiment of the present invention, $cumEO_x$ is at least 0.8 kton ethylene oxide/m$^3$ catalyst greater than $cumEO_1$, preferably at least 1.0 kton ethylene oxide/m$^3$ catalyst greater than $cumEO_1$ and the optimum overall catalyst chloriding effectiveness value of the inlet feed gas $Cl_{eff_x}$ at said cumulative EO production $cumEO_x$ is such that the ratio of $Cl_{eff_x}/Cl_{eff_1}$ is in the range of from 0.8 to 1.2, preferably in the range of from 0.9 to 1.1.

In a further preferred embodiment of the present invention, as cumulative ethylene oxide production increases from $cumEO_1$ to $cumEO_x$, the ratio of $Cl_{eff_x}/Cl_{eff_1}$ is maintained throughout the period of said increase in the range of from 0.8 to 1.2, more preferably in the range of from 0.9 to 1.1.

In a particularly preferred embodiment of the present invention, as cumulative ethylene oxide production increases from $cumEO_1$ to reach its final value of $cumEO_x$ at the end of catalyst life, the ratio of $Cl_{eff_x}/Cl_{eff_1}$ is maintained throughout the entire life of the catalyst in the range of from 0.8 to 1.2, preferably in the range of from 0.9 to 1.1.

For the avoidance of doubt, in the process of the present invention, aspects of the afore-mentioned preferred embodiments may be present alone or in combination.

Optionally, the inlet feed gas may further comprise carbon dioxide. When present, carbon dioxide is typically present in the inlet feed gas in a concentration of 0.10 mole-% or greater, relative to the total inlet feed gas, or 0.12 mole-% or greater, or 0.15 mole-% or greater, or 0.17 mole-% or greater, or 0.20 mole-% or greater, or 0.22 mole-% or greater, or 0.25 mole-% or greater, on the same basis. Similarly, carbon dioxide is generally present in the inlet feed gas in a concentration of at most 10 mole-%, relative to the total inlet feed gas, or at most 8 mole-%, or at most 5 mole-%, or at most 3 mole-%, or at most 2.5 mole-%, on the same basis. In some embodiments, carbon dioxide may be present in the inlet feed gas in a concentration of from 0.10 mole-% to 10 mole-%, relative to the total inlet feed gas, or from 0.15 mole-% to 5 mole-%, or from 0.20 mole-% to 3 mole-%, or from 0.25 mole-% to 2.5 mole-%, on the same basis.

As previously mentioned, carbon dioxide is produced as a reaction by-product and is typically introduced into the inlet feed gas via the use of a recycle gas stream in the epoxidation process. Carbon dioxide generally has an adverse effect on catalyst performance, with the operating temperature increasing as the concentration of carbon dioxide present in the inlet feed gas increases. Accordingly, in the commercial production of ethylene oxide, it is common for at least a portion of the carbon dioxide to be continuously removed from the recycle gas stream (e.g., via a carbon dioxide separation system) to maintain the concentration of carbon dioxide in the inlet feed gas at an acceptable level.

Optionally, the inlet feed gas further comprises water vapor. Water vapor may be present in the inlet feed gas in a concentration in the range of from 0 mole-% to 3 mole-%, relative to the total inlet feed gas, preferably in the range of from 0.1 mole-% to 2 mole-% and more preferably in the range of from 0.2 mole-% to 1 mole-%, on the same basis.

The inlet feed gas optionally may further comprise a dilution gas, such as nitrogen, methane, or a combination thereof. When used, a dilution gas may be added to the inlet feed gas to increase the oxygen flammability concentration. If desired, a dilution gas may be present in the inlet feed gas in a concentration of at least 5 mole-%, relative to the total inlet feed gas, or at least 10 mole-%, or at least 20 mole-%, or at least 25 mole-%, or at least 30 mole-%, on the same basis. Similarly, a dilution gas may be present in the inlet feed gas in a concentration of at most 80 mole-%, relative to the total inlet feed gas, or at most 75 mole-%, or at most 70 mole-%, or at most 65 mole-%, on the same basis. In some embodiments, a dilution gas may be present in the inlet feed gas in a concentration of from 20 mole-% to 80 mole-%, relative to the total inlet feed gas, or from 30 mole-% to 70 mole-%, on the same basis.

Furthermore, as previously mentioned, the inlet feed gas may further comprise one or more impurities, such as argon, ethane, etc. As will be understood by one of skill in the art, the type and concentration of impurities present in the inlet feed gas are determined, at least in part, by the purity of the oxygen and ethylene that is supplied to the epoxidation reactor and the extent to which any such impurities are removed during the epoxidation process.

The order and manner in which the components of the inlet feed gas are combined prior to contacting the epoxidation catalyst is not limited, and they may be combined simultaneously or sequentially. However, as will be recognized by one skilled in the art, it may be desirable to combine certain components of the inlet feed gas in a specified order for safety reasons. For example, oxygen may be added to the inlet feed gas after the addition of a dilution gas for safety reasons. Similarly, as will be understood by one of skill in the art, the concentration of various feed components present in the inlet feed gas may be adjusted throughout the epoxidation process, for example, to maintain a desired productivity, optimize the epoxidation process, etc. Accordingly, the above-defined concentration ranges were selected to cover the widest possible variations in inlet feed gas composition during normal operation.

Operating Conditions

The epoxidation process of the present invention may be carried out under a broad range of operating conditions that may vary widely between different ethylene oxide plants depending, at least in part, upon the initial plant design, subsequent expansion projects, feedstock availability, the type of epoxidation catalyst used, process economics, etc. Examples of such operating conditions include, but are not limited to, feed gas composition, reactor inlet pressure, gas flow through the epoxidation reactor (commonly expressed as the gas hourly space velocity or "GHSV"), and the ethylene oxide production parameter (i.e., ethylene oxide production rate, ethylene oxide production rate/catalyst volume (work rate) or product gas ethylene oxide concentration).

To achieve reasonable commercial ethylene oxide production rates, the epoxidation reaction is typically carried out at a reaction temperature of 180° C. or higher, or 190° C. or higher, or 200° C. or higher, or 210° C. or higher, or 225° C. or higher. Similarly, the reaction temperature is typically 325° C. or lower, or 310° C. or lower, or 300° C.

or lower, or 280° C. or lower, or 260° C. or lower. The reaction temperature may be from 180° C. to 325° C., or from 190° C. to 300° C., or from 210° C. to 300° C. It should be noted that the term "reaction temperature" as used herein refers to any selected temperature(s) that are directly or indirectly indicative of the catalyst bed temperature. For example, the reaction temperature may be a catalyst bed temperature at a specific location in the catalyst bed or a numerical average of several catalyst bed temperature measurements made along one or more catalyst bed dimensions (e.g., along the length). Alternatively, the reaction temperature may be, for example, the gas temperature at a specific location in the catalyst bed, a numerical average of several gas temperature measurements made along one or more catalyst bed dimensions, the gas temperature as measured at the inlet or outlet of the epoxidation reactor, a numerical average of several coolant temperature measurements made along one or more catalyst bed dimensions, or the coolant temperature as measured at the outlet of the epoxidation reactor. One example of a well-known device used to measure the reaction temperature is a thermocouple.

For the avoidance of doubt, the present invention is independent of the specific method chosen by any ethylene oxide plant operator to determine the reaction temperature. The only requirement is that once chosen, the method to determine reaction temperature should be consistently applied throughout the life of the catalyst.

In the present invention, there is a cumulative ethylene oxide production, $cumEO_1$, of at least 0.2 kton ethylene oxide/$m^3$ catalyst, prefer ably at least: 0.25 kton ethylene oxide/$m^3$ catalyst and more preferably at least 0.3 kton ethylene oxide/$m^3$ catalyst, at the point in time when said process is operating at a reaction temperature having a value $T_1$.

The reaction temperature $T_1$ is preferably at a value in the range of from 180 to 260° C., more preferably in the range of from 195 to 250° C. and most preferably in the range of from 210 to 240° C.

In the process of the present invention, as the epoxidation catalyst ages over time, the reaction temperature is increased to a value $T_x$ to maintain said ethylene oxide production parameter at a value $EO_1$ whilst the optimum overall catalyst chloriding effectiveness value of the inlet feed gas $Cl_{eff_x}$ is controlled such that the ratio of $Cl_{eff_x}/Cl_{eff_1}$ is in the range of from 0.8 to 1.2, preferably in the range of from 0.9 to 1.1.

Hence, said process is subsequently operated such that at a cumulative ethylene oxide production $cumEO_x$, wherein $cumEO_x$ is at least 0.6 kton ethylene oxide/$m^3$ catalyst, preferably at least 0.8 kton ethylene oxide/$m^3$ catalyst and more preferably at least 1.0 kton ethylene oxide/$m^3$ catalyst, greater than $cumEO_1$, the reaction temperature has an increased value $T_x$ to maintain said ethylene oxide production parameter at a value $EO_1$ whilst the optimum overall catalyst chloriding effectiveness value of the inlet feed gas $Cl_{eff_x}$ is controlled such that the ratio of $Cl_{eff_x}/Cl_{eff_1}$ is in the range of from 0.8 to 1.2, preferably in the range of from 0.9 to 1.1.

The reaction temperature $T_x$ is preferably at a value in the range of from 200 to 300° C., more preferably in the range of from 210 to 290° C. and most preferably in the range of from 220 to 280° C.

The epoxidation processes disclosed herein are typically carried out at a reactor inlet pressure of from 1000 to 3000 kPa, or from 1200 to 2500 kPa, absolute. A variety of well-known devices may be used to measure the reactor inlet pressure, for example, pressure-indicating transducers, gauges, etc., may be employed. It is within the ability of one skilled in the art to select a suitable reactor inlet pressure, taking into consideration, for example, the specific type of epoxidation reactor, desired productivity, etc.

The gas flow through the epoxidation reactor is expressed in terms of the Gas Hourly Space Velocity ("GHSV"), which is the quotient of the volumetric flow rate of the inlet feed gas at normal temperature and pressure (e.g., 0° C., 1 atm) divided by the catalyst bed volume (i.e., the volume of the epoxidation reactor that contains epoxidation catalyst). GHSV represents how many times per hour the inlet feed gas would displace the volume of the epoxidation reactor if the gas were at normal temperature and pressure (e.g., 0° C., 1 atm). Generally, as GHSV increases, catalyst selectivity increases. However, for a fixed catalyst volume, increasing GHSV generally leads to increased energy costs; therefore, there is usually an economic trade-off between higher catalyst selectivity and increased operating costs. Typically, in a gas phase epoxidation process, the GHSV is from 1,500 to 10,000 per hour.

The ethylene oxide production parameter is typically described in terms of work rate, which refers to the amount of ethylene oxide produced per hour per unit volume of catalyst. As is known to those skilled in the art, work rate is a function of several different variables, including, but not limited to, reactor temperature, reactor pressure, GHSV, and the composition of the inlet feed gas (e.g., ethylene concentration, oxygen concentration, carbon dioxide concentration, etc.). In general, for a given set of conditions, increasing the reaction temperature at those conditions increases the work rate, resulting in increased ethylene oxide production. However, this increase in temperature often reduces catalyst selectivity and may accelerate the aging of the catalyst. On the other hand, as an epoxidation catalyst undergoes natural catalyst aging over time, the work rate will gradually decrease at a constant reaction temperature. Under such circumstances, reaction temperature is increased in order to maintain work rate at the required value. Typically, the work rate in most reactors is from 50 to 600 kg of ethylene oxide per $m^3$ of catalyst per hour (kg/$m^3$/h), for example, from 50 to 400 kg/$m^3$/h or from 120 to 350 kg/$m^3$/h.

One skilled in the art with the benefit of the present disclosure will be able to select appropriate operating conditions, such as reaction temperature, reactor inlet pressure, GHSV, and work rate depending upon, for example, plant design, equipment constraints, the inlet feed gas composition, the age of the epoxidation catalyst, etc.

Ethylene oxide produced by the epoxidation processes disclosed herein may be recovered using methods known in the art. In some embodiments, the ethylene oxide may be further reacted with water, an alcohol, carbon dioxide or an amine according to known methods to form ethylene glycol, an ethylene glycol ether, ethylene carbonate or ethanolamine, respectively, if desired.

Hence, the process of the present invention may further comprise reacting at least a portion of the ethylene oxide produced with at least one reagent selected from the group consisting of: water, an alcohol, carbon dioxide and an amine to form ethylene glycol, an ethylene glycol ether, ethylene carbonate and ethanolamine, respectively.

The conversion into 1,2-ethanediol (ethylene glycol) or the 1,2-ethanediol ether (ethylene glycol ether) may comprise, for example, reacting ethylene oxide with water, suitably using an acidic or a basic catalyst. For example, for making predominantly 1,2-ethanediol and less 1,2-ethanediol ether, the ethylene oxide may be reacted with a ten-fold molar excess of water, in a liquid phase reaction in presence of an acid catalyst, e.g. 0.5 to 1.0% w sulfuric acid, based on the total reaction mixture, at a temperature of 50° C. to 70° C. and a pressure of 1 bar absolute, or in a gas phase reaction at 130° C. to 240° C. and a pressure of 20 to 40 bar absolute, preferably in the absence of a catalyst. Generally, if the proportion of water is lowered, the proportion of 1,2-ethanediol ethers in the reaction mixture increases. The 1,2-ethanediol ethers thus produced may be a di-ether, tri-ether, tetra-ether or a subsequent ether. Alternative 1,2-ethanediol ethers may be prepared by converting the ethylene oxide with an alcohol, in particular a primary alcohol, such as methanol or ethanol, by replacing at least a portion of the water by the alcohol.

The conversion into ethanolamine may comprise, for example, reacting ethylene oxide with ammonia. Anhydrous or aqueous ammonia may be used, although anhydrous ammonia is typically used to favor the production of monoethanolamine. For methods applicable in the conversion of the ethylene oxide into ethanolamine, reference may be made to, for example, U.S. Pat. No. 4,845,296 A, which is incorporated herein by reference.

Ethylene glycol and ethylene glycol ether may be used in a large variety of industrial applications, for example in the fields of food, beverages, tobacco, cosmetics, thermoplastic polymers, curable resin systems, detergents, heat transfer systems, etc. Ethylene carbonate may be used as, for example, a precursor in the manufacture of ethylene glycol, or as a diluent, in particular as a solvent. Ethanolamine may be used, for example, in the treating ("sweetening") of natural gas.

Epoxidation Catalysts

Epoxidation catalysts suitable for use in the processes described herein comprise a fluoride-mineralized alpha-alumina carrier, and deposited on said carrier, silver, a rhenium promoter, one or more alkali metal promoters and optionally, one or more of a co-promoter and/or one or more of a further metal promoter.

Detailed information on the fluoride-mineralized alpha-alumina carrier and epoxidation catalysts comprising the fluoride-mineralized alpha-alumina carrier to be used in the process of the present invention are provided below.

For the avoidance of doubt, aspects of the preferred embodiments of said carrier and catalyst described hereinbelow may be used alone or in combination in the process of the present invention.

Preparation of Fluoride-Mineralized Alpha-Alumina Carrier

In general, fluoride-mineralized alpha-alumina carriers used in the catalysts for the process of the present invention are prepared by calcining alpha-alumina precursor(s) in the presence of a fluoride mineralizing agent. The particular manner in which the fluoride-mineralized alpha-alumina carrier is prepared is not limited, and therefore any method known in the art for preparing fluoride-mineralized alpha-alumina carriers may be used, such as those methods described in U.S. Pat. Nos. 3,950,507 A, 4,379,134 A, 4,994,588 A, 4,994,589 A and 6,203,773 B1, US 2012/0108832 A1 and US 2018/0161761 A1, which are incorporated herein by reference, for descriptions relating to the mineralization of alpha-alumina.

One method for preparing the fluoride-mineralized alpha-alumina carrier comprises combining alpha-alumina precursor(s) with a fluoride mineralizing agent and calcining the combination. The alpha-alumina precursor(s) may be combined with the fluoride mineralizing agent by any method known in the art. Further, the alpha-alumina precursor(s) and the fluoride mineralizing agent, along with any other desired raw materials, may be provided in any form and combined in any order. For example, alpha-alumina precursor(s) are typically formed into a formed body (e.g., a solid that has been formed into a selected shape suitable for its intended use) and the fluoride mineralizing agent may be combined with the alpha-alumina precursor(s) at any point prior to, during, or after the formation of such formed body and likewise, at any point prior to or during calcination. For example, in some instances, alpha-alumina precursor(s) may be combined with a solution comprising a fluoride mineralizing agent, the combination may be mixed and formed into a formed body (e.g., extruded), and the formed body calcined to form the fluoride-mineralized alpha-alumina carrier. Alternatively, alpha-alumina precursor(s) may first be formed into a formed body and then the formed body may be combined with a fluoride mineralizing agent (e.g., by impregnating the formed body with a solution comprising a fluoride mineralizing agent), and subsequently calcined to form the fluoride-mineralized alpha-alumina carrier. Furthermore, in other instances, alpha-alumina precursor(s) may be formed into a formed body and then contacted with a fluoride-mineralizing agent during calcination (e.g., by calcining the formed body in a gaseous atmosphere comprising the fluoride mineralizing agent). Accordingly, any known preparative method may be used, provided that the alpha-alumina precursor(s) are calcined in the presence of a fluoride mineralizing agent.

With regards to suitable alpha-alumina precursors, any material that is capable of being at least partially converted to alpha-alumina when heated at a temperature of 1200° C. or less may be used. For example, suitable alpha-alumina precursors include, but are not limited to, aluminum trihydroxides, such as gibbsite, bayerite, and nordstrandite; aluminum oxide hydroxides, such as boehmite, pseudoboehmite and diaspora; transition aluminas, such as gamma-alumina, delta-alumina, eta-alumina, kappa-alumina, chi-alumina, rho-alumina, and theta-alumina; and a combination thereof. As previously mentioned, alpha-alumina precursors may be in any form. Typically, alpha-alumina precursor(s) are included in an amount sufficient to provide, after calcination, a fluoride-mineralized alpha-alumina carrier that comprises at least 80% by weight, or at least 85% by weight, or at least 90% by weight, or at least 95% by weight alpha-alumina, or up to 99.9% by weight, or to 100% by weight alpha-alumina.

As will be recognized by one skilled in the art, variations in the particulate size(s) of the alumina-alumina precursor(s) used has an effect on the physical characteristics of the resulting fluoride-mineralized alpha-alumina carrier, such as pore size distribution and total pore volume. Similarly, as will be understood by one of skill in the art, the level of impurities present in the fluoride-mineralized alpha-alumina carrier are determined, at least in part, by the purity of the alpha-alumina precursor(s) that are used (along with any other raw materials), the degree of volatilization of impurities during calcination, and whether any impurities are removed during any subsequent wash and/or treatment procedures. Common impurities may include silica, alkali and alkaline earth metal oxides and trace amounts of metal and/or non-metal containing additives.

With regards to suitable fluoride mineralizing agents, any material that is volatile or which can be readily volatilized under calcining conditions of the alpha-alumina precursor(s) may be used. Preferably, the fluoride mineralizing agent is capable of providing a volatile fluorine species at a temperature of 1200° C. or less, typically from 800° C. to 1200° C. Fluoride mineralizing agents may be organic or inorganic and may include ionic, covalent, and polar covalent compounds. The specific form in which a fluoride mineralizing agent is provided is not limited and therefore, a volatile fluorine species may include fluorine, fluoride ions and fluorine-containing compounds. Similarly, the fluoride mineralizing agent may be provided in gaseous or liquid solution (e.g., provided in the form of a solution comprising the fluoride mineralizing agent), or in gaseous form. Examples of suitable fluoride mineralizing agents include, but are not limited to, $F_2$, aluminum trifluoride ($AlF_3$), ammonium fluorides, such as ammonium bifluoride ($NH_4HF_2$) and ammonium fluoride ($NH_4F$), hydrogen fluoride, hydrofluoric acid, dichlorodifluoromethane ($CCl_2F_2$), silicon tetrafluoride ($SiF_4$), silicon hexafluoride ($[SiF_6]_2$—), boron trifluoride ($BF_3$), nitrogen trifluoride ($NF_3$), xenon difluoride ($XeF_2$), sulfur hexafluoride ($SF_6$), phosphorous pentafluoride ($PF_5$), carbon tetrafluoride ($CF_4$), fluoroform ($CHF_3$), tetrafluoroethane ($C_2H_2F_4$), trifluoroacetic acid, triflic acid, hexafluorosilicates, hexafluorophosphates, tetrafluoroaluminates, alkali metal (Group 1) fluorides, alkaline earth metal (Group 2) fluorides, Group 4 metal fluorides, Group 6 metal fluorides, Group 8-13 metal fluorides, lanthanide fluorides, and a combination thereof.

Generally, a fluoride mineralizing agent is used in an amount of at least 0.10% by weight, calculated as the weight of elemental fluorine used relative to the total weight of alpha-alumina precursor(s), and any optional additives, to which the fluoride mineralizing agent is being added. Preferably, the fluoride mineralizing agent is used in an amount no less than 0.20% by weight, more preferably no less than 0.25% by weight. Typically, the fluoride mineralizing agent is used in an amount up to 5% by weight, or up 3% by weight, or up to 2.5% by weight. Although it is possible to use a fluoride mineralizing agent in excess of 5% by weight, such amounts are not generally employed as they are considered unnecessary. These amounts refer to the amount of fluoride mineralizing agent used to prepare the fluoride-mineralized alpha-alumina carrier and do not necessarily reflect the amount that may ultimately be present in the fluoride-mineralized alpha-alumina carrier, as such amounts will vary depending upon the specific process conditions under which the fluoride-mineralized alpha-alumina carrier was made (e.g., calcining temperature, rate of heating, the type and amount of alpha alumina precursor that is used, calcination atmosphere, etc.). Reference is made to, for example, Shaklee, et al, "*Growth of α-Al₂O₃ Platelets in the HF-γ-Al₂O₃ System*", Journal of the American Ceramic Society, Volume 77, No. 11 (1994), pp. 2977-2984 for further discussion relating to the effects of fluoride concentration on carrier properties.

If desired, one or more optional additives may be included when preparing the fluoride-mineralized alpha-alumina carrier. For example, it may be desirable to include one or more additives to facilitate in forming a formed body and/or to alter one or more of the characteristics of the resulting fluoride-mineralized alpha-alumina carrier. Suitable additives may include any of the wide variety of known carrier additives, which include, but are not limited to, bonding agents (e.g., polyolefin oxides, celluloses, alkaline earth metal compounds, such as magnesium silicate and calcium silicate, and alkali metal compounds), extrusion aids (e.g., petroleum jelly, hydrogenated oil, synthetic alcohol, synthetic ester, glycol, starch, polyolefin oxide, polyethylene glycol, and mixtures thereof), solvents (e.g., water), peptizing acids (e.g., an inorganic acid (such as nitric acid), a monofunctional aliphatic carboxylic acid containing from 1 to about 5 carbon atoms (such as acetic acid, propanoic acid and formic acid), a halogenated monofunctional aliphatic carboxylic acid containing from 1 to about 5 carbon atoms (such as mono-, di-, and trichloro acetic acid), etc.), fluxing agents, binders, dispersants, burnout materials (also known as "pore formers"), strength-enhancing additives, etc. Additionally, in some embodiments, alpha-alumina may be included as an additive. It is within the ability of one skilled in the art to select suitable additives in appropriate amounts, taking into consideration, for example, the preparation method and the desired properties of the resulting fluoride-mineralized alpha-alumina carrier. Furthermore, alpha-alumina precursor(s) and any other desired additives may be in any form and combined in any order, i.e., the order of addition of alpha-alumina precursor(s) and any other additives is not critical.

Burnout materials may optionally be included when preparing the fluoride-mineralized alpha-alumina carrier to facilitate the shaping of a formed body and/or to alter the porosity of a resulting fluoride-mineralized alpha-alumina carrier. Typically, burnout materials are burned out, sublimed, or volatilized during drying or calcining. Examples of suitable burnout materials include, but are not limited to, comminuted shells of nuts such as pecan, cashew, walnut, peach, apricot and filbert, and granulated polyolefins, such as polyethylene and polypropylene.

A strength-enhancing additive may optionally be included in the fluoride-mineralized alpha-alumina carrier, for example, to increase the crush strength and/or improve the attrition resistance of the fluoride-mineralized alpha-alumina carrier. Reference is made to U.S. Pat. No. 7,560,411 B2, U.S. Pat. No. 8,513,156 B2, U.S. Pat. No. 8,536,083 B2 and U.S. Pat. No. 8,603,937 B2, which are incorporated herein by reference, for descriptions relating to strength-enhancing additives. Examples of suitable strength-enhancing additives may include, but are not limited to, a zirconium species, a lanthanide Group species, a Group 2 metal species, an inorganic glass, or mixtures thereof. The specific form in which the strength-enhancing additive exists prior to being incorporated into the fluoride-mineralized alpha-alumina carrier is not limited. Thus, a zirconium species, a lanthanide Group species, and a Group 2 metal species includes any specific element as such and compounds of the element. Additionally, the strength-enhancing additive may be used in the form of a composition comprising the strength-enhancing additive, such as a solution or emulsion comprising the strength-enhancing additive. Illustrative strength-enhancing additives include, but are not limited to, ammonium fluorozirconate, calcium zirconate, zirconium acetate, zirconium acetylacetonate, zirconium carbonate, zirconium fluoride, zirconium oxynitrate, zirconium silicate, lanthanum carbonate, lanthanum fluoride, lanthanum nitrate, lanthanum oxalate, lanthanum oxide, cerium carbonate, cerium fluoride, cerium nitrate, cerium oxalate, cerium oxide, magnesium acetate, magnesium carbonate, magnesium fluoride, magnesium nitrate, magnesium oxalate, magnesium oxide, calcium acetate, calcium carbonate, calcium fluoride, calcium nitrate, calcium oxalate, and calcium oxide. In some embodiments, a strength-enhancing additive may be included in an amount of 0.10% by weight to 5% by weight, calculated as the amount of the element used relative to the total weight of alpha-alumina precursor(s), and any optional additives, to which the strength-enhancing additive is being added.

In those embodiments wherein the strength-enhancing additive comprises inorganic glass, it is preferable that the inorganic glass has a melting temperature that is at most the temperature at which the calcination is carried out. For example, the inorganic glass may have a melting temperature that is below 1200° C. Melting temperature of the inorganic glass is understood to mean the temperature at which the ingredients of the inorganic glass would be heated during glass manufacture to obtain a fluid. Typical inorganic glass may include the elements silicon, boron, aluminum, or lead in combination with many other elements, such as alkali and alkaline earth metals. These elements are typically employed as their oxides. Illustrative inorganic glass that may be used for purposes of the present disclosure include, among many others, the following: $Na_2O·SiO_2+Na_2O·2SiO_2$, $Na_2O·2SiO_2+SiO_2$ (quartz), $K_2O·SiO_2+K_2O·2SiO_2$, $K_2O·2SiO_2+K_2O·4SiO_2$, PbO, $2PbO·SiO_2+PbO·SiO_2$, $Na_2O·SiO_2+Na_2O·2SiO_2+2Na_2O·CaO·3SiO_2$, $K_2O·2SiO_2+K_2O·2CaO·9SiO_2+K_2O·4SiO_2$, $Na_2O·4B_2O_3+SiO_2$, and $Na_2O·2B_2O_3+Na_2O·SiO_2$.

Optionally, a potassium compound may be included when preparing the fluoride-mineralized alpha-alumina carrier. It may be desirable to include a potassium compound, for example, to form a melt with a low melting point during the calcination. Suitable potassium compounds may include potassium-containing inorganic or organic compounds, such as an inorganic acid salt, an organic acid salt or a hydroxide of potassium and the like, for example, potassium nitrate, potassium nitrite, potassium carbonate, potassium bicarbonate, potassium fluoride, potassium sulfate, potassium stearate, potassium silicate, potassium oxalate, potassium acetate, potassium hydroxide, potassium meta-aluminate. In some embodiments, a potassium compound may be included in an amount of 0.01 to 3% by weight, calculated as the amount of potassium used relative to the total weight of alpha-alumina precursor(s), and any optional additives, to which the potassium compound is being added.

Typically, alpha-alumina precursor(s), and optionally a fluoride mineralizing agent and/or one or more additives, are formed into a formed body prior to calcination. The manner in which a formed body is prepared is not limited and may include any of several known methods. In some embodiments, a formed body may be prepared from a malleable mixture of raw materials comprising alpha-alumina precursor(s), and optionally the fluoride mineralizing agent and/or one or more additives. The malleable mixture of raw materials may be prepared according to any of several known methods (e.g., ball milling, mix-mulling, ribbon blending, vertical screw mixing, V-blending, attrition milling, etc.) and subsequently formed into a formed body by any of several known methods (e.g., extrusion, spraying, spray drying, agglomeration, pressing, injection molding, slip casting, tape casting, roll compaction, etc.). The malleable mixture (e.g., dough, paste, etc.) may be prepared dry (i.e., in the absence of a liquid medium) or wet. For applicable methods, reference may be made to U.S. Pat. Nos. 5,145,824 A, 5,512,530 A, 5,384,302 A, 5,100,859 A and 5,733,842 A, which are herein incorporated by reference.

Once formed, a formed body may optionally be heated under an atmosphere sufficient to remove water, decompose any organic additives, or otherwise modify the formed body prior to calcination. Suitable atmospheres include, but are not limited to, air, nitrogen, argon, hydrogen, carbon dioxide, water vapor, those comprising fluorine-containing gases or combinations thereof. If desired, such heating is generally conducted at a temperature in the range of from 20° C. to 500° C. and preferably between 30° C. and 300° C., typically for a period of time of at least one minute up to 100 hours and preferably from 5 minutes to 50 hours. Vessels suitable for drying are generally known in the art and may be the same or different than the vessel used for calcination.

Calcination is generally conducted at a temperature that is high enough, and for a period of time that is sufficiently long enough, to induce mineralization of at least a portion of the alpha-alumina precursor(s). In particular, calcination may be conducted at one or more temperatures, at one or more pressures, and for one or more time periods, sufficient to convert at least 50%, or at least 75%, or at least 85%, or at least 90% or at least 95% of the alpha-alumina precursor(s) to alpha-alumina. Calcining may be carried out in any suitable atmosphere, including but not limited to, air, nitrogen, argon, helium, carbon dioxide, water vapor, those comprising a fluoride mineralizing agent and a combination thereof. However, in those embodiments where a formed body further comprises an organic burnout material, at least one of heating and/or calcining is at least partially or entirely carried out in an oxidizing atmosphere, such as in an oxygen-containing atmosphere.

Calcining generally occurs at a temperature of 1200° C. or less, and preferably occurs at a temperature of 750° C. or greater, and even more preferably at a temperature of 900° C. or greater. It is generally desirable to maintain the calcination temperature at 1200° C. or less to prevent excessive amounts of fluoride from being liberated, as this may have a detrimental effect on the morphology of the fluoride-mineralized alpha-alumina carrier. The pressure during calcination may be any pressure, including sub atmospheric, atmospheric and super atmospheric pressure. Preferably, calcination is conducted at atmospheric pressure. Depending upon the calcination temperature, calcining typically occurs for a period of time of up to 5 hours, preferably from 0.5 to 3 hours, at atmospheric pressure. As would be recognized by one skilled in the art, if calcining is conducted at a lower temperature, a longer period of time is generally required for the mineralization process and likewise, if calcining is conducted at a higher temperature, the mineralization process typically requires less time.

While it is provided herein that calcination should generally be conducted at a temperature that is high enough, and for a period of time that is sufficiently long enough, to induce mineralization of at least a portion of the alpha-alumina precursor(s) (e.g., at a temperature in a range of from 750° C. to 1200° C., for a period of time from 0.5 to 3 hours, and at atmospheric pressure), the present disclosure is nevertheless independent of the manner by which calcination is conducted. Thus, variations in calcining known in the art, such as holding at one temperature for a certain period of time and then raising the temperature to a second temperature over the course of a second period of time, are contemplated by the present disclosure. Similarly, it should be noted that the surface properties of the resulting fluoride-mineralized alpha-alumina carrier depend not only on the calcining temperature but also, at least in part, on the rate of heating during calcination. It is within the ability of one skilled in the art to select suitable calcination conditions, taking into consideration, for example, the desired properties of the resulting fluoride-mineralized alpha-alumina carrier. Reference is made to, for example, U.S. Pat. No. 4,379,134 A, and Daimon, et al., "*Morphology of Corundum Crystallized by Heating Mixture of $η-Al_2O_3$ and $AlF_3$*", Journal of Crystal Growth, Volume 75 (1986), pp. 348-352 for further discussion relating to the effects of temperature on the mineralization process.

With respect to suitable vessels for calcining, such vessels are generally known in the art. The specific vessel in which calcining is performed is not limited, and therefore any suitable vessel known in the art may be used. Examples of such vessels include, but are not limited to, furnaces, such as a static kiln, a rotary kiln, etc. Furthermore, the temperature and pressure within such vessel may be measured by any suitable means.

After calcining, the resulting fluoride-mineralized alpha-alumina carrier may optionally be washed and/or treated prior to deposition of the catalytic material (e.g., silver). Likewise, if desired, any raw materials used to form the fluoride-mineralized alpha-alumina carrier may be washed and/or treated prior to calcination. Any method known in the art for washing and/or treating may be used in accordance with the present disclosure, provided that such method does not negatively affect the performance of the resulting epoxidation catalyst. Reference is made to U.S. Pat. No. 6,368,998 B1, U.S. Pat. No. 7,232,918 B2 and U.S. Pat. No. 7,741,499 B2 which are incorporated herein by reference, for descriptions relating to such methods. If washing is desired, it is typically conducted at a temperature in the range of from 15° C. to 120° C. and for a period of time up to 100 hours and preferably from 5 minutes to 50 hours. Washing may be conducted in either a continuous or batch fashion.

Examples of suitable washing solutions may include, but are not limited, water (e.g., deionized water), aqueous solutions comprising one or more salts (e.g., ammonium salts), amine solutions (e.g., ethylenediamine), aqueous organic diluents and a combination thereof. Similarly, suitable aqueous solutions may be acidic, basic or neutral. The volume of washing solution may be such that the fluoride-mineralized alpha-alumina carrier is impregnated until a point of incipient wetness of the carrier has been reached. Alternatively, a larger volume may be used and the surplus of solution may be removed from the wet carrier, for example, by centrifugation. Furthermore, following any washing and/or treating step, it is preferable, prior to deposition of the catalytic material (e.g., silver), to dry or roast the fluoride-mineralized alpha-alumina carrier. For example, the carrier may be dried in a stream of air, for example at a temperature of from 80° C. to 400° C., for a sufficient period of time.

Fluoride-mineralized alpha-alumina carriers are commercially available from carrier manufacturers.

Fluoride-Mineralized Alpha-Alumina Carrier—Physical Properties

Fluoride-mineralized alpha-alumina carriers suitable for use herein may be selected from those having a varied and wide range of physical properties, including shape, size, packing density, surface area, water absorption, crush strength, attrition resistance, total pore volume, median pore diameter, pore size distributions, etc.

In a preferred embodiment, the fluoride-mineralized alpha-alumina carrier has a particulate matrix having a lamellar or platelet-type morphology. More preferably, the lamellar or platelet-type morphology is such that particles having in at least one direction a size greater than 0.1 micrometer have at least one substantially flat major surface.

Suitable shapes for the fluoride-mineralized alpha-alumina carrier include any of the wide variety of shapes known for carriers, which include, but are not limited to, pills, chunks, tablets, pieces, pellets, rings, spheres, wagon wheels, trapezoidal bodies, doughnuts, amphora, rings, Raschig rings, honeycombs, monoliths, saddles, cylinders, hollow cylinders, multi-lobed cylinders, cross-partitioned hollow cylinders (e.g., cylinders having at least one partition extending between walls), cylinders having gas channels from side wall to side wall, cylinders having two or more gas channels, and ribbed or finned structures. While the cylinders are often circular, other cross-sections, such as oval, hexagonal, quadrilateral, trilateral, and multi-lobed may be useful. Preferably, the fluoride-mineralized alpha-alumina carrier is multi-lobed. Reference may be made to US 2012/0171407 A1 incorporated by reference herein, for further description of multi-lobed carriers.

Additionally, the size of the fluoride-mineralized alpha-alumina carrier is generally not limited, and may include any size suitable for use in an epoxidation reactor. For example, the fluoride-mineralized alpha-alumina carrier may be in the shape of a cylinder having a length of 5 to 15 millimeters ("mm"), an outside diameter of 5 to 15 mm, and an inside diameter of 0.2 to 4 mm. In some embodiments, the fluoride-mineralized alpha-alumina carrier may have a length-to-outside diameter ratio of 0.8 to 1.2. Additionally, the fluoride-mineralized alpha-alumina carrier may be in the shape of a hollow cylinder with a wall thickness of 1 to 7 mm. It is within the ability of one skilled in the art, with the benefit of this disclosure, to select a suitable shape and size of the fluoride-mineralized alpha-alumina carrier, taking into consideration, for example, the type and configuration of the epoxidation reactor in which the fluoride-mineralized alpha-alumina carrier will be employed (e.g., the length and internal diameter of the tubes within the epoxidation reactor).

In general, the surface area of a carrier is indicative of the amount of surface area per gram of carrier that is available for the deposition of catalytic material (e.g., silver). The surface area of the fluoride-mineralized alpha-alumina carrier suitable for use herein is not narrowly critical and may be, for example, from 0.1 to 10 $m^2/g$, relative to the weight of the fluoride-mineralized alpha-alumina carrier, or from 0.5 to 5 $m^2/g$, or from 0.7 to 3 $m^2/g$, or at least 0.1 $m^2/g$, or at least 0.3 $m^2/g$, or at least 0.5 $m^2/g$, or at least 0.6 $m^2/g$, or at most 10 $m^2/g$, or at most 5 $m^2/g$, or at most 3 $m^2/g$, on the same basis. As used herein, "surface area" is understood to refer to the surface area of the fluoride-mineralized alpha-alumina carrier as measured in accordance with the B.E.T. (Brunauer, Emmett and Teller) method as described in detail in Brunauer, S., Emmet, P. Y. and Teller, E., J. Am. Chem. Soc., 60, 309-16 (1938).

The water absorption of a carrier is typically expressed as the weight of water than can be absorbed into the pores of the carrier, relative to the weight of the carrier, and therefore reported as grams of water per gram of carrier and the units may be abbreviated as "g/g". Typically, the water absorption of the fluoride-mineralized alpha-alumina carrier suitable for use herein may be, for example, from 0.2 to 1.2 g/g, relative to the weight of the fluoride-mineralized alpha-alumina carrier, or from 0.3 g/g, or at least 0.2 g/g, or at least 0.3 g/g, or at most 0.8 g/g, or at most 0.7 g/g, on the same basis. As used herein, the term "water absorption" is understood to refer to the water absorption of a carrier as measured in accordance with the following procedure: First, approximately 100 g of representative samples of fluoride-mineralized alpha-alumina carrier are dried at 110° C. for a minimum of one hour. The samples are then cooled in a desiccator and the dry weight (D) of each sample is then determined to the nearest 0.01 g. The samples are then placed in a pan of distilled water and boiled for thirty minutes. While the water is boiling, the samples are covered with water and setter pins or some similar device are used to separate the samples from the bottom and sides of the pan and from each other. After the thirty minute boil, the samples are transferred to room temperature water and allowed to soak for an additional fifteen minutes. After returning to room temperature, each sample is then blotted lightly with a moistened, lint-free linen or cotton cloth to remove all excess water from the surface and the saturated weight (M)

of each sample is determined to the nearest 0.01 g. The blotting operation may be accomplished by rolling the specimen lightly on the wet cloth which shall previously have been saturated with water and then pressed only enough to remove such water as will drip from the cloth. Excessive blotting should be avoided because it will introduce error by withdrawing water from the pores of the sample. The samples should be weighed immediately after blotting. The entire operation should be completed as quickly as possible to minimize errors caused by evaporation of water from the sample. Water absorption (A) is expressed as the weight of water absorbed, relative to the weight of the dried carrier and is determined using the following formula: A=[(M−D)/D] wherein the water absorption is expressed in units of grams of water per gram of carrier ("g/g"). Water absorption may also be expressed in units of "cc/g", provided there is a correction for the density of water at the conditions measured. Alternatively, when water absorption is measured according to the above described procedure, it may be convenient to express the water absorption in units of grams of water absorbed per 100 grams of carrier (e.g., 60 g/100 g), which may also be expressed as the weight percentage of water absorbed per 100 g of carrier (e.g., 60%). The water absorption of a carrier may be positively correlated to and thus used interchangeably with the term "porosity" which, in the field of catalyst carriers, is usually understood to mean the carrier's open cell porosity. Generally, as the water absorption of a carrier increases, the ease of deposition of catalytic material on the carrier increases. However, at higher water absorptions, the fluoride-mineralized alpha-alumina carrier, or an epoxidation catalyst comprising the carrier, may have lower crush strength or attrition resistance.

The crush strength of a carrier is typically expressed as the amount of compressive force required to crush the carrier, relative to the length of the carrier, and therefore reported as the amount of force per millimeter of carrier and the units may be abbreviated as "N/mm". The crush strength of a fluoride-mineralized alpha-alumina carrier suitable for use herein is not narrowly critical, although it should have a crush strength sufficient to allow for its use in the commercial production of ethylene oxide. Typically, the crush strength of a fluoride-mineralized alpha-alumina carrier suitable for use herein may be, for example, at least 1.8 N/mm, or at least 2 N/mm, or at least 3.5 N/mm, or at least 5 N/mm and frequently as much as 40 N/mm, or as much as 25 N/mm, or as much as 15 N/mm. As used herein, the term "crush strength" is understood to refer to the crush strength of a carrier as measured in accordance with ASTM D6175-03, wherein the test sample is tested as such after its preparation, that is with elimination of Step 7.2 of said method, which represents a step of drying the test sample. For this crush strength test method, the crush strength of the carrier is typically measured as the crush strength of hollow cylindrical particles of 8.8 mm external diameter, 3.5 mm internal diameter, and 8 mm length.

In general, the attrition resistance of a carrier is indicative of the propensity of the carrier to produce fines in the course of transportation, handing and use. The attrition resistance of a fluoride-mineralized alpha-alumina carrier suitable for use herein is not narrowly critical, although it should be sufficiently robust so to allow for its use in the commercial production of ethylene oxide. Typically, a fluoride-mineralized alpha-alumina carrier suitable for use herein may exhibit an attrition of at most 50%, or at most 40%, or at most 30% and is typically at least 5%, or at least 10%, or at least 15%, or at least 20%. As used herein, "attrition resistance" is understood to refer to the attrition resistance of a carrier as measured in accordance with ASTM D4058-92, wherein the test sample is tested as such after its preparation, that is with elimination of Step 6.4 of the said method, which represents a step of drying the test sample. For this test method, the attrition resistance of the carrier is typically measured as the attrition resistance of hollow cylindrical particles of 8.8 mm external diameter, 3.5 mm internal diameter, and 8 mm length.

The total pore volume, the median pore diameter, and the pore size distribution of a carrier may be measured by a conventional mercury intrusion porosimetry device in which liquid mercury is forced into the pores of a carrier. Greater pressure is needed to force the mercury into the smaller pores and the measurement of pressure increments corresponds to volume increments in the pores penetrated and hence to the size of the pores in the incremental volume. As used herein, the pore size distribution, the median pore diameter and the pore volumes are as measured by mercury intrusion porosimetry to a pressure of $2.1 \times 10^8$ Pa using a Micromeritics Autopore 9200 model (130° contact angle, mercury with a surface tension of 0.480 N/m, and correction for mercury compression applied). As used herein, the median pore diameter is understood to mean the pore diameter corresponding to the point in the pore size distribution at which 50% of the total pore volume is found in pores having less than (or greater than) said point.

The total pore volume of a fluoride-mineralized alpha-alumina carrier suitable for use herein is not narrowly critical and may be, for example, at least 0.20 mL/g, at least 0.30 mL/g, at least 0.40 mL/g, at least 0.50 mL/g and is typically at most 0.80 mL/g, at most 0.75 mL/g, or at most 0.70 mL/g. Generally, as the total pore volume of a carrier increases, the ability to deposit catalytic material on the carrier increases. However, at higher total pore volumes, the fluoride-mineralized alpha-alumina carrier, or an epoxidation catalyst comprising the carrier, may have lower crush strength or attrition resistance. The median pore diameter of a fluoride-mineralized alpha-alumina carrier suitable for use herein is not narrowly critical and may be, for example, from 0.50 to 50 μm. In addition, fluoride-mineralized alpha-alumina carriers suitable for use herein may have a pore size distribution that is monomodal, bimodal or multimodal.

As will be understood by one of skill in the art, the catalytic performance of an epoxidation catalyst comprising a fluoride-mineralized alpha-alumina carrier will generally vary depending upon the particular physical properties of the fluoride-mineralized alpha-alumina carrier used. Accordingly, the ranges disclosed herein with respect to such physical properties were selected to cover the widest possible variations in physical properties, the effects of which may be readily determined by experimentation.

Epoxidation Catalyst Composition

Epoxidation catalysts suitable for use herein comprise a fluoride-mineralized alpha-alumina carrier, as previously described above, and deposited on said carrier, silver, a rhenium promoter, and one or more alkali metal promoters. Optionally, said epoxidation catalyst may further comprise one or more of a co-promoter, one or more of a further metal promoter, and/or a combination thereof. As used herein, the term "optional promoter(s)" refers to one or more of a co-promoter, one or more of a further metal promoter and any combination thereof.

In broad terms, silver is deposited onto the fluoride-mineralized alpha-alumina carrier in an amount sufficient to catalyze the vapor phase reaction of ethylene with oxygen to produce ethylene oxide. When epoxidation catalysts comprising different amounts of silver are prepared on carriers of similar packing densities, it is convenient to compare the epoxidation catalysts on a silver weight basis, which is typically expressed in weight percent silver as a function of the total weight of the epoxidation catalyst. As used herein, unless otherwise specified, the total weight of the epoxidation catalyst is understood to refer to the weight of the fluoride-mineralized alpha-alumina carrier and all components deposited thereon, including silver, rhenium promoter, alkali metal promoter and any optional promoter(s).

Typically, epoxidation catalysts suitable for use herein comprise silver in an amount of 1 to 55% by weight, relative to the total weight of the epoxidation catalyst, or from 1 to 50% by weight, or from 5 to 40% by weight, or from 8 to 35% by weight, or from 10 to 30% by weight, or at least 10% by weight, or at least 15% by weight, or at most 45% by weight, or at most 40% by weight, on the same basis. The upper and lower limits of suitable amounts of silver can be suitably varied, depending upon the particular catalytic performance characteristics or effect desired or the other variables involved, including economic factors.

Alternatively, the amount of silver included in an epoxidation catalyst can be expressed in terms of mass of silver per unit volume of epoxidation catalyst loaded into an epoxidation reactor (e.g., into the catalyst bed). In this way, comparisons of silver loadings between epoxidation catalysts prepared on fluoride-mineralized alpha-alumina carriers of different packing densities can be made. Ultimately, the catalyst bed contains a defined volume of epoxidation catalyst, so this method of comparing the amount of silver deposited on an epoxidation catalyst is appropriate. Accordingly, epoxidation catalysts suitable for use herein may comprise silver in an amount of at least 50 kg/m$^3$, relative to the total volume of epoxidation catalyst loaded into the catalyst bed, or at least 100 kg/m$^3$, or at least 125 kg/m$^3$, or at least 150 kg/m$^3$, on the same basis. Similarly, epoxidation catalysts suitable for use herein may comprise silver in an amount of at most 500 kg/m$^3$, relative to the total volume of epoxidation catalyst loaded into the catalyst bed, or at most 450 kg/m$^3$, or at most 400 kg/m$^3$, or at most 350 kg/m$^3$, on the same basis. Preferably, epoxidation catalysts comprise silver in an amount of from 50 to 500 kg/m$^3$, relative to the total volume of epoxidation catalyst loaded into the catalyst bed, or from 100 to 450 kg/m$^3$, or from 125 to 350 kg/m$^3$, on the same basis.

In addition to silver, epoxidation catalysts suitable for use herein further comprise a rhenium promoter, an alkali metal promoter and optionally, one or more a co-promoter, one or more of a further metal promoter and/or a combination thereof.

Suitable alkali metal promoters for use in the epoxidation catalyst may be selected from the group consisting of lithium, sodium, potassium, rubidium, cesium, and a combination thereof. Suitable co-promoters may be selected from the group consisting of sulfur, phosphorus, boron, tungsten, molybdenum, chromium, and a combination thereof. Suitable further metal promoters may include an alkaline earth metal (e.g., beryllium, magnesium, calcium, strontium, barium, etc.), titanium, hafnium, zirconium, vanadium, thallium, thorium, tantalum, niobium, gallium, germanium, manganese and a combination thereof.

During the reaction to make ethylene oxide, the specific form of the rhenium promoter, alkali metal promoter, co-promoter and further metal promoter may be unknown.

In general, the specific form in which a rhenium promoter, one or more alkali metal promoters and optional promoter(s) is provided is not limited, and may include any of the wide variety of forms known. For example, a rhenium promoter, one or more alkali metal promoters and optional promoter(s) may suitably be provided as ions (e.g., cation, anion, oxyanion, etc.), or as compounds (e.g., rhenium salts, salts of a co-promoter, alkali metal salts, salts of a further metal promoter, etc.). Generally, suitable compounds are those which can be solubilized in an appropriate solvent, such as a water-containing solvent. As used herein, the term "compound" refers to the combination of a particular element with one or more different elements by surface and/or chemical bonding, such as ionic and/or covalent and/or coordinate bonding. The term "ion" or "ionic" refers to an electrically chemical charged moiety; "cation" or "cationic" being positive, "anion" or "anionic" being negative, and "oxyanion" or "oxyanionic" being a negatively charged moiety containing at least one oxygen atom in combination with another element (i.e., an oxygen-containing anion). It is understood that ions do not exist in vacuo, but are found in combination with charge-balancing counter ions when added. The term "oxidic" refers to a charged or neutral species wherein an element in question is bound to oxygen and possibly one or more different elements by surface and/or chemical bonding, such as ionic and/or covalent and/or coordinate bonding. Thus, an oxidic compound is an oxygen-containing compound which also may be a mixed, double or complex surface oxide. Illustrative oxidic compounds include, but are not limited to, oxides (containing only oxygen as the second element), hydroxides, nitrates, sulfates, carboxylates, carbonates, bicarbonates, oxyhalides, etc. as well as surface species wherein the element in question is bound directly or indirectly to an oxygen either in the substrate or the surface.

As will be appreciated by those of skill in the art, while a specific form of a rhenium promoter, an alkali metal promoter or optional promoter(s) may be provided during catalyst preparation, it is possible that during the conditions of preparation of the epoxidation catalyst and/or during use in the epoxidation process, the particular form initially present may be converted to another form. Indeed, once deposited on the fluoride-mineralized alpha-alumina carrier and/or during use of the epoxidation catalyst, the specific form of the rhenium promoter, alkali metal promoter or optional promoter(s) is not always known. Furthermore, in many instances, analytical techniques may not be sufficient to precisely identify the form that is present. Accordingly, the present disclosure is not intended to be limited by the exact form of the rhenium promoter, alkali metal promoter and/or optional promoter(s) that may ultimately exist on the epoxidation catalyst during use. Additionally, it should be understood that while a particular compound may be used during catalyst preparation (e.g., cesium hydroxide is added to an impregnation solution), it is possible that the counter ion added during catalyst preparation may not be present in the finished epoxidation catalyst (e.g., an epoxidation catalyst made using an impregnation solution comprising cesium hydroxide may be analyzed to contain cesium but not hydroxide in the finished epoxidation catalyst).

Epoxidation catalysts suitable for use herein may comprise a rhenium promoter deposited on a fluoride-mineralized alpha-alumina carrier in an amount of 0.01 to 50 mmole/kg, calculated as the amount of rhenium relative to the total weight of the epoxidation catalyst, or from 0.1 to 50 mmole/kg, or from 0.1 to 25 mmole/kg, or from 0.1 to 20 mmole/kg, or from 0.5 to 10 mmole/kg, or from 1 to 6 mmole/kg, or at least 0.01 mmole/kg, or at least 0.1 mmole/kg, or at least 0.5 mmole/kg, or at least 1 mmole/kg, or at least 1.25 mmole/kg, or at least 1.5 mmole/kg, or at most 50 mmole/kg, or at most 20 mmole/kg, or at most 10 mmole/kg, or at most 6 mmole/kg, on the same basis. Alternatively stated, the amount of rhenium promoter, expressed relative to the surface area of the fluoride-mineralized alpha-alumina carrier, may preferably be present in the epoxidation catalyst in an amount of from 0.25 to 10 $\mu$mole/m$^2$, or from 0.5 to 5 $\mu$mole/m$^2$, or from 1 to 3 $\mu$mole/m$^2$. For purposes of convenience, the amount of rhenium promoter deposited on the epoxidation catalyst is measured as the metal, irrespective of the form in which it is present.

The degree of benefit obtained within the above-defined concentration limits will vary depending upon one or more properties and characteristics, such as, for example, epoxidation conditions, catalyst preparative conditions, the physical properties and surface chemical properties of the carrier utilized, the amount of silver deposited on the epoxidation catalyst, the amount of alkali metal promoter deposited, the amount (if any) of optional promoter(s) deposited, and the amount of other cations and anions present in the epoxidation catalyst, either alone or in combination with the rhenium promoter, the alkali metal promoter and/or optional promoter(s). Accordingly, the above-defined limits were selected to cover the widest possible variations in properties and characteristics.

As previously discussed, the specific form in which a rhenium promoter is provided is generally not limited, and may include any of the wide variety of forms known. For example, the rhenium promoter may be provided as the metal, as an ion (e.g., cation, anion, oxyanion, etc.), or as a rhenium compound. Examples of suitable rhenium compounds include, but are not limited to, rhenium salts such as rhenium halides, rhenium oxyhalides, the rhenates, the perrhenates (e.g., ammonium perrhenate, alkali metal perrhenates, alkaline earth metal perrhenates, silver perrhenate, etc.), the oxides and the acids of rhenium. Specific examples of rhenium compounds include, but are not limited to, Re$_2$O$_7$, HReO$_4$, NH$_4$ReO$_4$, LiReO$_4$, NaReO$_4$, KReO$_4$, RbReO$_4$, CsReO$_4$, and a combination thereof. It should be understood that there are many rhenium compounds that are not soluble per se in water. However, these compounds can be solubilized by utilizing various acids, bases, peroxides, alcohols, etc. After solubilization these compounds could be used, for example, with an appropriate amount of water or other suitable solvent to provide a rhenium promoter. Of course, it is also understood that upon solubilization of many of these compounds, the original compound no longer exists after solubilization. For example, rhenium metal is not soluble in water. However, it is soluble in concentrated nitric acid as well as in hydrogen peroxide solution. Thus, by using an appropriate reactive solvent one could use rhenium metal to provide the rhenium promoter.

Epoxidation catalysts suitable for use herein may further comprise the alkali metal promoter (i.e., lithium, sodium, potassium, rubidium, cesium, or a combination thereof) deposited on a fluoride-mineralized alpha-alumina carrier in an amount of 0.01 to 500 mmole/kg, calculated as the amount of the element relative to the total weight of the epoxidation catalyst, or from 0.01 to 400 mmole/kg, or from 0.1 to 300 mmole/kg, or from 0.1 to 250 mmole/kg, or from 0.5 to 200 mmole/kg, or from 1 to 100 mmole/kg, or at least 0.01 mmole/kg, or at least 0.05, or at least 0.1 mmole/kg, or at least 0.5 mmole/kg, or at least 1 mmole/kg, or at least 1.25 mmole/kg, or at least 1.5 mmole/kg, or at least 2 mmole/kg, or at least 3 mmole/kg, or at most 500 mmole/kg, or at most 400 mmole/kg, or at most 300 mmole/kg, or at most 250 mmole/kg, or at most 200 mmole/kg, or at most 150 mmole/kg, or at most 100 mmole/kg, on the same basis. For purposes of convenience, the amount of the alkali metal deposited on the epoxidation catalyst is measured as the element, irrespective of the form in which it is present.

It should be understood that the amount of alkali metal promoter deposited on the fluoride-mineralized alpha-alumina carrier is not necessarily the total amount of alkali metal present in the epoxidation catalyst. Rather, the amount deposited reflects the amount of alkali metal promoter that has been added to the fluoride-mineralized alpha-alumina carrier (e.g., via impregnation). As such, the amount of alkali metal promoter deposited on the fluoride-mineralized alpha-alumina carrier does not include any amount of alkali metals that may be locked into the carrier, for example, by calcining, or are not extractable in a suitable solvent such as water or lower alkanol or amine or mixtures thereof and do not provide a promoting effect. It is also understood that the source of the alkali metal promoter may be the fluoride-mineralized alpha-alumina carrier itself. That is, the fluoride-mineralized alpha-alumina carrier may contain extractable amounts of an alkali metal promoter that can be extracted with a suitable solvent, such as water or lower alkanol, thus preparing a solution from which the alkali metal promoter may be deposited or redeposited on the fluoride-mineralized alpha-alumina carrier.

The degree of benefit obtained within the above-defined concentration limits will vary depending upon one or more properties and characteristics, such as, for example, epoxidation conditions, catalyst preparative conditions, the physical properties and surface chemical properties of the carrier utilized, the amount of silver deposited on the epoxidation catalyst, the amount of rhenium promoter deposited on the epoxidation catalyst, the amount (if any) of a co-promoter and/or further metal promoter deposited on the epoxidation catalyst, and the amount of other cations and anions present in the epoxidation catalyst, either alone or in combination with the rhenium promoter and/or optional promoter(s). Accordingly, the above-defined limits were selected to cover the widest possible variations in properties and characteristics.

As previously discussed, the specific form in which an alkali metal promoter is provided is generally not limited, and may include any of the wide variety of forms known. For example, the alkali metal promoter may be provided as an ion (e.g., cation), or as an alkali metal compound. Examples of suitable alkali metal compounds include, but are not limited to, alkali metal salts and oxidic compounds of the alkali metals, such as the nitrates, nitrites, carbonates, bicarbonates, oxalates, carboxylic acid salts, hydroxides, halides, oxyhalides, borates, sulfates, sulfites, bisulfates, acetates, tartrates, lactates, oxides, peroxides, and iso-propoxides, etc.

As previously mentioned, the alkali metal promoter may comprise a combination of two or more alkali metal promoters. Non-limiting examples include a combination of cesium and rubidium, a combination of cesium and potassium, a combination of cesium and sodium, a combination of cesium and lithium, a combination of cesium, rubidium and sodium, a combination of cesium, potassium and sodium, a combination of cesium, lithium and sodium, a combination of cesium, rubidium and sodium, a combination of cesium, rubidium, potassium and lithium, and a combination of cesium, potassium, and lithium.

Furthermore, in those embodiments where an epoxidation catalyst comprises a combination of two or more alkali metal promoters, it may be particularly beneficial if the alkali metal promoters comprise potassium and at least one additional alkali metal promoter selected from cesium, rubidium, and a combination thereof, preferably cesium. The amount of potassium deposited on the fluoride-mineralized alpha-alumina carrier may be in an amount of 0.01 to 50 mmole/kg, calculated as the amount of the element relative to the total weight of the epoxidation catalyst, or from 0.1 to 400 mmole/kg, or from 0.2 to 30 mmole/kg, or from 0.5 to 20 mmole/kg, or from 1 to 15 mmole/kg, or from 1.5 to 10 mmole/kg, or from 2 to 8 mmole/kg, or at least 0.01 mmole/kg, or at least 0.1 mmole/kg, or at least 0.2, or at least 0.5 mmole/kg, or at least 1 mmole/kg, or at least 1.25 mmole/kg, or at least 1.5 mmole/kg, or at least 1.75 mmole/ kg, or at least 2 mmole/kg, or at least 3 mmole/kg, or at most 40 mmole/kg, or at most 35 mmole/kg, or at most 30 mmole/kg, or at most 25 mmole/kg, or at most 20 mmole/kg, or at most 15 mmole/kg, or at most 10 mmole/kg, on the same basis. The amount of the at least one additional alkali metal promoter selected from cesium, rubidium, and a combination thereof deposited on the fluoride-mineralized alpha-alumina carrier may be in an amount of 0.1 to 40 mmole/kg, calculated as the amount of the element (e.g., cesium and/or rubidium) relative to the total weight of the epoxidation catalyst, or from 0.2 to 35 mmole/kg, or from 0.25 to 30 mmole/kg, or from 0.5 to 20 mmole/kg, or from 1 to 15 mmole/kg, or from 3 to 10 mmole/kg, or at least 0.1 mmole/kg, or at least 0.15, or at least 0.2 mmole/kg, or at least 0.25 mmole/kg, or at least 0.3 mmole/kg, or at least 0.35 mmole/kg, or at least 0.4 mmole/kg, or at least 0.45 mmole/kg, or at least 0.5 mmole/kg, or at most 40 mmole/ kg, or at most 35 mmole/kg, or at most 30 mmole/kg, or at most 25 mmole/kg, or at most 20 mmole/kg, or at most 15 mmole/kg, or at most 10 mmole/kg, on the same basis. Further, it may be beneficial to deposit the potassium and the at least one additional alkali metal promoter selected from cesium, rubidium, and a combination thereof in an amount such that the molar ratio of potassium to the additional alkali metal promoter is at least 0.25, or at least 0.5, at least 0.75, at least 1, or at least 1.25, or at most 20, at most 15, at most 10, or at most 7.5, or at most 5.

Further, in those embodiments where the alkali metal promoter comprises a combination of potassium and at least one additional alkali metal promoter selected from cesium, rubidium, and a combination thereof, it may be additionally advantageous to deposit a third alkali metal promoter selected from the group consisting of lithium, sodium and a combination thereof, preferably lithium. The amount of the third alkali metal promoter selected from lithium, sodium and a combination thereof deposited on the fluoride-mineralized alpha-alumina carrier may be in an amount of 0.1 to 400 mmole/kg, calculated as the amount of the element (e.g., lithium and/or sodium) relative to the total weight of the epoxidation catalyst, or from 0.5 to 350 mmole/kg, or from 1 to 300 mmole/kg, or from 1 to 200 mmole/kg, or from 1 to 150 mmole/kg, or from 5 to 100 mmole/kg, or at least 0.1 mmole/kg, or at least 0.1, or at least 0.25 mmole/kg, or at least 0.5 mmole/kg, or at least 0.75 mmole/kg, or at least 1 mmole/kg, or at least 2.5 mmole/kg, or at least 5 mmole/kg, or at most 400 mmole/kg, or at most 350 mmole/kg, or at most 300 mmole/kg, or at most 250 mmole/kg, or at most 200 mmole/kg, or at most 150 mmole/kg, or at most 100 mmole/kg, on the same basis.

Further, in those embodiments where the alkali metal promoter comprises potassium, it may be particularly advantageous if the fluoride-mineralized alpha-alumina carrier contains nitric acid leachable potassium in a quantity of less than 85 parts per million by weight ("ppmw"), relative to the weight of the fluoride mineralized carrier, or less than 80 ppmw, less than 75 ppmw, or less than 65 ppmw, on the same basis. The quantity of nitric acid leachable potassium is deemed to be the quantity insofar as it can be extracted from the fluoride-mineralized alpha-alumina carrier. The extraction involves extracting a 10-gram sample of the fluoride-mineralized alpha-alumina carrier with 100 mL of 10% w nitric acid for 30 minutes at 100° C. (1 atm) and determining the amount of potassium present in the extract using standard Atomic Absorption spectroscopy techniques. Similarly, in those embodiments where the alkali metal promoter comprises potassium, it may also be advantageous if the fluoride-mineralized alpha-alumina carrier contains water leachable potassium in a quantity of less than 40 ppmw, relative to the weight of the fluoride-mineralized alpha-alumina carrier, less than 35 ppmw, or less than 30 ppmw, on the same basis. The quantity of water leachable potassium in the fluoride-mineralized alpha-alumina carrier is deemed to be the quantity insofar as it can be extracted from the fluoride-mineralized alpha-alumina carrier. The extraction involves extracting a 2-gram sample of the fluoride-mineralized alpha-alumina carrier three times by heating it in 25-gram portions of de-ionized water for 5 minutes at 100 C and determining in the combined extracts the amount of alkali metal by using a known method, for example atomic absorption spectroscopy.

In these embodiments, potassium may be deposited in a quantity of at least 0.5 mmole/kg, at least 1 mmole/kg, at least 1.5 mmole/kg, at least 1.75 mmole/kg, calculated as the total quantity of the potassium deposited relative to the weight of the catalyst. Similarly, potassium may be deposited in an amount of at most 20 mmole/kg, at most 15 mmole/kg, at most 10 mmole/kg, at most 5 mmole/kg, on the same basis. Potassium may be deposited in an amount in the range of from 0.5 to 20 mmole/kg, from 1 to 15 mmole/kg, from 1.5 to 7.5 mmole/kg, from 1.75 to 5 mmole/kg, on the same basis. Additionally, it may be advantageous, if the epoxidation catalyst comprises potassium in an amount such that the amount of water extractable potassium of the catalyst may be at least 1.25 mmole/kg, relative to the weight of the epoxidation catalyst, at least 1.5 mmole/kg, or at least 1.75 mmole/kg, on the same basis. Suitably, the epoxidation catalyst may comprise water extractable potassium in an amount of at most 10 mmole/kg, at most 7.5 mmole/kg, at most 5 mmole/kg, on the same basis. Suitably, the epoxidation catalyst may comprise water extractable potassium in an amount in the range of from 1.25 to 10 mmole/kg, from 1.5 to 7.5 mmole/kg, or from 1.75 to 5 mmole/kg, on the same basis. The source of water extractable potassium may originate from the fluoride-mineralized alpha-alumina carrier and/or the components of the epoxidation catalyst. The quantity of water extractable potassium in the catalyst is deemed to be the quantity insofar as it can be extracted from the catalyst. The extraction involves extracting a 2-gram sample of the catalyst three times by heating it in 25-gram portions of de-ionized water for 5 minutes at 100 C and determining in the combined extracts the amount of potassium by using a known method, for example atomic absorption spectroscopy.

Optionally, epoxidation catalysts suitable for use herein may further comprise a co-promoter (e.g., sulfur, phosphorus, boron, tungsten, molybdenum, chromium, or a combination thereof) deposited on a fluoride-mineralized alpha-alumina carrier in an amount of 0.01 to 500 mmole/kg, calculated as the amount of the element relative to the total weight of the epoxidation catalyst, or from 0.01 to 100 mmole/kg, or from 0.1 to 50 mmole/kg, or from 0.1 to 20 mmole/kg, or from 0.5 to 10 mmole/kg, or from 1 to 6 mmole/kg, or at least 0.01 mmole/kg, or at least 0.05, or at least 0.1 mmole/kg, or at least 0.5 mmole/kg, or at least 1 mmole/kg, or at least 1.25 mmole/kg, or at least 1.5 mmole/kg, or at least 2 mmole/kg, or at least 3 mmole/kg, or at most 100 mmole/kg, or at most 50 mmole/kg, or at most 40 mmole/kg, or at most 30 mmole/kg, or at most 20 mmole/kg, or at most 10 mmole/kg, or at most 5 mmole/kg, on the same basis. For purposes of convenience, the amount of co-promoter deposited on the epoxidation catalyst is measured as the element, irrespective of the form in which it is present.

The degree of benefit obtained within the above-defined concentration limits will vary depending upon one or more properties and characteristics, such as, for example, epoxidation conditions, catalyst preparative conditions, the physical properties and surface chemical properties of the carrier utilized, the amount of silver deposited on the epoxidation catalyst, the amount of rhenium promoter and alkali metal promoter deposited on the epoxidation catalyst, the amount (if any) of further metal promoter deposited on the epoxidation catalyst, and the amount of other cations and anions present in the epoxidation catalyst, either alone or in combination with the rhenium promoter, co-promoter, alkali metal promoter and/or further metal promoter. Accordingly, the above-defined limits were selected to cover the widest possible variations in properties and characteristics.

As previously discussed, the specific form in which a co-promoter is provided is generally not limited, and may include any of the wide variety of forms known. For example, the co-promoter may be provided as an ion (e.g., cation, anion, oxyanion, etc.), or as a co-promoter compound (e.g., salts of the co-promoters). Examples of suitable co-promoter compounds include, but are not limited to, salts of the co-promoter elements, such as the oxyanionic compounds of the co-promoter elements (e.g., ammonium oxyanionates, such ammonium sulfate, ammonium molybdate, etc.; alkali metal oxyanionates, such as potassium sulfate, cesium chromate, rubidium tungstate, lithium sulfate, sodium tungstate, lithium chromate, etc.). Specific examples of anions of sulfur that can be suitably applied include sulfate, sulfite, bisulfite, bisulfate, sulfonate, persulfate, thiosulfate, dithionate, dithionite, etc. Specific examples of anions of phosphorus and boron that can be suitably applied include phosphate, polyphosphates, etc.; and borates, etc. Specific examples of anions of molybdenum, tungsten and chromium that can be suitably applied include molybdate, dimolybdate, paramolybdate, other iso- and hetero-polymolybdates, etc.; tungstate, paratungstate, metatungstate, other iso- and hetero-polytungstates, etc.; and chromate, dichromate, chromite, halochromate, etc. The anions can be supplied with various counter-ions (e.g., ammonium, alkali metal, alkaline earth metal, and hydrogen (i.e., acid form)). The anions can be prepared by the reactive dissolution of various non-anionic materials, such as the oxides (e.g., SO$_2$, SO$_3$, MoO$_3$, WO$_3$, Cr$_2$O$_3$, etc.), as well as other materials such as halides, oxyhalides, hydroxyhalides, hydroxides, sulfides, etc., of the co-promoter elements.

In those embodiments where the epoxidation catalyst for use in the present invention comprises a co-promoter, it may be particularly beneficial if the co-promoter comprises a combination of a first co-promoter selected from the group consisting of sulfur, phosphorus, boron, and a combination thereof, and a second co-promoter selected from the group consisting of tungsten, molybdenum, chromium, and a combination thereof.

The amount of the first co-promoter deposited on the fluoride-mineralized alpha-alumina carrier may be in an amount of 0.2 to 50 mmole/kg, calculated as the amount of the element (e.g., sulfur, phosphorus and/or boron) relative to the total weight of the epoxidation catalyst, or from 0.5 to 45 mmole/kg, or from 0.5 to 30 mmole/kg, or from 1 to 20 mmole/kg, or from 1.5 to 10 mmole/kg, or from 2 to 6 mmole/kg, or at least 0.2 mmole/kg, or at least 0.3, or at least 0.5 mmole/kg, or at least 1 mmole/kg, or at least 1.25 mmole/kg, or at least 1.5 mmole/kg, or at least 1.75 mmole/kg, or at least 2 mmole/kg, or at least 3 mmole/kg, or at most 50 mmole/kg, or at most 45 mmole/kg, or at most 40 mmole/kg, or at most 35 mmole/kg, or at most 30 mmole/kg, or at most 20 mmole/kg, or at most 10 mmole/kg, or at most 6 mmole/kg, on the same basis. The amount of the second co-promoter deposited on the fluoride-mineralized alpha-alumina carrier may be in an amount of 0.1 to 40 mmole/kg, calculated as the amount of the element (e.g., tungsten, molybdenum and/or chromium) relative to the total weight of the epoxidation catalyst, or from 0.15 to 30 mmole/kg, or from 0.2 to 25 mmole/kg, or from 0.25 to 20 mmole/kg, or from 0.3 to 10 mmole/kg, or from 0.4 mmole/kg to 5 mmole/kg, or at least 0.1 mmole/kg, or at least 0.15, or at least 0.2 mmole/kg, or at least 0.25 mmole/kg, or at least 0.3 mmole/kg, or at least 0.35 mmole/kg, or at least 0.4 mmole/kg, or at least 0.45 mmole/kg, or at least 0.5 mmole/kg, or at most 40 mmole/kg, or at most 35 mmole/kg, or at most 30 mmole/kg, or at most 25 mmole/kg, or at most 20 mmole/kg, or at most 15 mmole/kg, or at most 10 mmole/kg, or at most 5 mmole/kg, on the same basis. Further, it may be beneficial to deposit the first and second co-promoters in an amount such that the molar ratio of the first co-promoter to the second co-promoter is greater than 1, or at least 1.25, at least 1.5, at least 2, or at least 2.5. It is further preferred that the molar ratio of the first co-promoter to the second co-promoter is at most 20, at most 15, at most 10, or at most 7.5. Additionally, it is preferred that the molar ratio of the rhenium promoter to the second co-promoter may be greater than 1, at least 1.25, or at least 1.5. It is further preferred that the molar ratio of the rhenium promoter to the second co-promoter may be at most 20, at most 15, or at most 10.

Optionally, epoxidation catalysts suitable for use herein may additionally comprise a further metal promoter (e.g., an alkaline earth metal such as beryllium, magnesium, calcium, strontium, barium, etc., titanium, hafnium, zirconium, vanadium, thallium, thorium, tantalum, niobium, gallium, germanium, manganese, etc.) deposited on a fluoride-mineralized alpha-alumina carrier in an amount of 0.01 to 500 mmole/kg, calculated as the amount of the element relative to the total weight of the epoxidation catalyst, or from 0.01 to 100 mmole/kg, or from 0.1 to 50 mmole/kg, or from 0.1 to 20 mmole/kg, or from 0.5 to 10 mmole/kg, or from 1 to 6 mmole/kg, or at least 0.01 mmole/kg, or at least 0.05, or at least 0.1 mmole/kg, or at least 0.5 mmole/kg, or at least 1 mmole/kg, or at least 1.25 mmole/kg, or at least 1.5 mmole/kg, or at least 2 mmole/kg, or at least 3 mmole/kg, or at most 100 mmole/kg, or at most 50 mmole/kg, or at most 40 mmole/kg, or at most 30 mmole/kg, or at most 20 mmole/kg, or at most 10 mmole/kg, or at most 5 mmole/kg, on the same basis. For purposes of convenience, the amount of further metal promoter in the epoxidation catalyst is measured as the element, irrespective of the form in which it is present.

The degree of benefit obtained within the above-defined concentration limits will vary depending upon one or more properties and characteristics, such as, for example, epoxidation conditions, catalyst preparative conditions, the physical properties and surface chemical properties of the carrier utilized, the amount of silver deposited on the epoxidation catalyst, the amount of rhenium promoter and alkali metal promoter deposited on the epoxidation catalyst, the amount (if any) of co-promoter deposited on the epoxidation catalyst, and the amount of other cations and anions present in the epoxidation catalyst, either alone or in combination with the rhenium promoter, alkali metal promoter and/or co-promoter. Accordingly, the above-defined limits were selected to cover the widest possible variations in properties and characteristics.

As previously discussed, the specific form in which a further metal promoter is provided is generally not limited, and may include any of the wide variety of forms known. For example, the further metal promoter may be provided as an ion (e.g., cation, anion, oxyanion, etc.), or as a compound (e.g., salts of the further metals). Examples of suitable compounds include, but are not limited to, salts of the further metals, such as alkaline earth metal salts (e.g., the nitrates, nitrites, carbonates, bicarbonates, oxalates, carboxylic acid salts, hydroxides, halides, oxyhalides, borates, sulfates, sulfites, bisulfates, acetates, tartrates, lactates and iso-propoxides, etc.), and the oxides, halides and oxyhalides of the further metals.

Well known methods can be employed to analyze for the amounts of silver, rhenium promoter, alkali metal promoter and optional promoter(s) deposited onto the fluoride-mineralized alpha-alumina carrier. The skilled artisan may employ, for example, material balances to determine the amounts of any of these deposited components. As an example, if the fluoride-mineralized alpha-alumina carrier is weighed prior to and after deposition of silver and a rhenium promoter, then the difference in the two weights will be equal to the amount of silver and the rhenium promoter deposited onto the fluoride-mineralized alpha-alumina carrier, from which the amount of the deposited rhenium promoter can be calculated. Additionally, the amount of the deposited silver and promoters can be calculated based upon the ratio of the concentration of silver and promoters included in the impregnation solution(s) and the total weight in the finished epoxidation catalyst.

Alternatively, the amount of promoters deposited on the fluoride-mineralized alpha-alumina carrier may also be determined by known leaching methods, wherein the amount of metallic leachables present in the fluoride-mineralized alpha-alumina carrier and the amount of metallic leachables present in the epoxidation catalyst are independently determined and the difference between the two measurements reflect the total amount of promoter deposited on the fluoride-mineralized alpha-alumina carrier. As an example, the amount of an alkali metal promoter deposited on an epoxidation catalyst may be determined by separately leaching a 10-gram sample of the fluoride-mineralized alpha-alumina carrier and a 10-gram sample of the epoxidation catalyst with 100 mL of 10% w nitric acid for 30 minutes at 100° C. (1 atm) and determining the amount of the alkali metal promoter present in the extracts using standard Atomic Absorption spectroscopy techniques. The difference in the measurements between the carrier and the catalyst reflect the amount of alkali metal promoter deposited onto the carrier.

Epoxidation Catalyst Preparation

The preparation of epoxidation catalysts comprising silver is known in the art. The specific manner in which epoxidation catalysts suitable for use herein are prepared is not limited, and therefore any method known in the art may be used. Reference is made to U.S. Pat. Nos. 4,761,394 A, 4,766,105 A, 5,380,697 A, 5,739,075 A, 6,368,998 B1 and 6,656,874 B2, which are incorporated herein by reference, for descriptions relating to the preparation of epoxidation catalysts.

In general, an epoxidation catalyst suitable for use herein is prepared by contacting (e.g., impregnating) a fluoride-mineralized alpha-alumina carrier with one or more solutions comprising silver, a rhenium promoter, an alkali metal promoter and, if desired, optional promoter(s); and subsequently depositing silver, the rhenium promoter, the alkali metal promoter and, if desired, any optional promoter(s), on the fluoride-mineralized alpha-alumina carrier, typically by heating the impregnated carrier.

As used herein, the phrase "contacting a fluoride-mineralized alpha-alumina carrier with one or more solutions comprising silver, a rhenium promoter, an alkali metal promoter and, if desired, optional promoter(s)" and similar or cognate terminology means that the fluoride-mineralized alpha-alumina carrier is contacted (e.g., impregnated) in a single step or multiple steps with one solution comprising silver, a rhenium promoter, an alkali metal promoter and, if desired, optional promoter(s); or in multiple steps with two or more solutions, wherein each solution comprises at least one component selected from silver, a rhenium promoter, an alkali metal promoter and, if desired, optional promoter(s), with the proviso that all of the components of silver, a rhenium promoter, an alkali metal promoter and if desired, optional promoter(s), will individually be found in at least one of the solutions. Furthermore, as is known in the art, the sequence of contacting the fluoride-mineralized alpha-alumina carrier with one or more solutions comprising silver, a rhenium promoter, an alkali metal promoter, and, if desired, optional promoter(s), as well as the sequence of depositing these components on the fluoride-mineralized alpha-alumina carrier, may vary. Thus, impregnation and deposition of silver, a rhenium promoter, an alkali metal promoter and if desired, optional promoter(s), may be effected coincidentally or sequentially. For example, a rhenium promoter, an alkali metal promoter and, if desired, optional promoter(s) may be deposited on a fluoride-mineralized alpha-alumina carrier either prior to, simultaneously with, or subsequent to the deposition of silver and each other. Similarly, the rhenium promoter, the alkali metal promoter and optional promoter(s) may be deposited together or sequentially. Furthermore, for example, silver may be deposited first followed by the coincidental or sequential deposition of a rhenium promoter, an alkali metal promoter and if desired, optional promoter(s); or alternatively, a rhenium promoter may be deposited first followed by coincidental or sequential deposition of silver, an alkali metal promoter and if desired, any optional promoter(s); or alternatively, an optional promoter may be deposited first followed by coincidental or sequential deposition of silver, a rhenium promoter, and an alkali metal promoter. If two or more impregnations are employed, the impregnated carrier is typically dried, or heated between each successive impregnation to ensure deposition of the components onto the carrier. Furthermore, if it is desired for the epoxidation catalyst to comprise silver in an amount greater than 25% by weight, it is often necessary to subject the fluoride-mineralized alpha-alumina carrier to at least two or more sequential impregnations of a solution comprising silver to obtain the desired amount of silver deposited on the carrier.

Although epoxidation catalysts suitable for use herein are typically prepared by impregnating a fluoride-mineralized alpha-alumina carrier with one or more solutions (commonly referred to as "impregnation solution(s)") comprising silver, a rhenium promoter, an alkali metal promoter, and, if desired, optional promoter(s), the present disclosure is not intended to be limited to any particular preparation method. Accordingly, any known preparative method may be used provided that the silver, rhenium promoter, alkali metal promoter, and optional promoter(s) (if any) are deposited on the fluoride-mineralized alpha-alumina carrier in a suitable manner. For example, alternatively, a coating of silver, rhenium promoter, alkali metal promoter, and if desired, optional promoter(s), may be formed on a fluoride-mineralized alpha-alumina carrier from one or more emulsions or slurries containing the components.

With regards to the specific form of silver used in the one or more solutions, any of the wide variety of forms known may be used, provided that the silver can be solubilized therein. For example, silver may suitably be provided as a silver compound, such as, a silver complex or a silver salt, such as silver nitrate, silver oxide, silver carbonate, and silver salts of mono- and polybasic carboxylic and hydroxy-carboxylic acids of up to 16 carbon atoms, such as silver acetate, propionate, butyrate, oxalate, malonate, malate, maleate, lactate, citrate, phthalate, higher fatty acids salts, and the like. Likewise, as previously mentioned, the specific form in which the rhenium promoter, alkali metal promoter and optional promoter(s) (if any) is provided is not critical, provided that they can be solubilized in an appropriate solvent and do not undesirably react with other components present in the solution. For example, when an alkali metal promoter is coincidentally deposited with silver, the alkali metal promoter employed is preferably one which does not react with the silver compound (e.g., silver salt) in solution in order to avoid premature silver precipitation from the same.

A wide variety of solvents or complexing/solubilizing agents may be employed in the one or more solutions to solubilize silver, the rhenium promoter, the alkali metal promoter and/or any optional promoter(s) to the desired concentration in the solution. The solvent used is not particularly limited and may include any solvent or agent capable of adequately dissolving the silver compound or converting the silver compound to a soluble form, or if the solution comprises a rhenium promoter, an alkali metal promoter and/or optional promoter(s), it should be capable of adequately dissolving or converting these components to a soluble form. Furthermore, suitable solvents or complexing/solubilizing agents should be capable of being readily removed in subsequent steps, either by a washing, volatilizing or oxidation procedure, or the like. Preferably, the solvent or complexing/solubilizing agent is readily miscible with water, as aqueous solutions may conveniently be employed. Examples of suitable solvents or complexing/solubilizing agents include, but are not limited to, alcohols, including glycols, such as ethylene glycol, ammonia, amines and aqueous mixtures of amines, carboxylic acids, such as lactic acid, and mixtures thereof. Additionally, examples of suitable amines include, but are not limited to, organic amines, such as, lower alkylenediamines of from 1 to 5 carbon atoms (e.g., ethylenediamine), mixtures of a lower alkanolamine of from 1 to 5 carbon atoms with a lower alkylenediamine of from 1 to 5 carbon atoms (e.g., ethylenediamine in combination with ethanolamine), as well as mixtures of ammonia with lower alkanolamines or lower alkylenediamines of from 1 to 5 carbons (e.g., ethanolamine in combination with ammonia, ethylenediamine in combination with ammonia). In those solutions comprising silver, these solubilizing/reducing agents are generally added in the amount of from 0.1 to 10 moles per mole of silver present.

Optionally, the one or more solutions may further comprise a base, such as a metal hydroxide (e.g., lithium hydroxide, cesium hydroxide, rubidium hydroxide, sodium hydroxide), an alkylammonium hydroxide (e.g., tetraalkylammonium hydroxides, such as tetramethylammonium hydroxide or tetraethylammonium hydroxide), 1,8-bis-(dimethylamino)-naphthalene, or a combination thereof, in an amount sufficient to provide a solution having a pH of above 11.2, more typically at least 11.7, preferably at least 12, as measured at 20° C. It should be understood that the pH of the solution may not be a true pH when the solution is not aqueous. Furthermore, if a base is included, it is often desirable to select a base that does not alter the metal concentration of the one or more solutions, such as an organic base; however, if changing the metals concentration of the solution is not a concern, metal bases may be used.

Following impregnation of the fluoride-mineralized alpha-alumina carrier with the one or more solutions, the carrier is typically separated from any remaining non-absorbed solution (e.g., by draining the excess solution, or by using separation techniques, such as filtration, centrifugation or evaporation under reduced pressure at a suitable temperature) and the silver, the rhenium promoter, the alkali metal promoter and, if desired, any optional promoter(s) are deposited on the carrier, most often by heating (also referred to as "roasting"). In general, the impregnated carrier is heated at a temperature that is high enough, and for a period of time that is sufficiently long enough, to cause reduction of the silver compound (e.g., silver complex) to metallic silver and to form a layer of finely divided silver, which is bound to the surface of the fluoride-mineralized alpha-alumina carrier, both the exterior and pore surface. It is observed that independent of the form in which the silver is present in the solution before precipitation on the fluoride-mineralized alpha-alumina carrier, the phrase "reduction of the silver compound to metallic silver" is used, while in the meantime often decomposition of the silver compound by heating occurs. The term "reduction" is preferably used herein in view of the conversion of the positively charged Ag+ ion into metallic Ag atom.

Generally, an impregnated carrier may be heated at a temperature of from 100° C. to 600° C. for a period of time ranging from 0.01 to 12 hours. The pressure during heating is preferably atmospheric pressure. As would be recognized by one skilled in the art, if heating is conducted at a lower temperature, a longer period of time is generally required and likewise, if heating is conducted at a higher temperature, less time is typically required. Although it is provided herein that heating should generally be conducted at a temperature in a range of from 100° C. to 600° C., for a period of time from 0.01 to 12 hours, and at atmospheric pressure, the present disclosure is nevertheless independent of the manner by which such heating is conducted. Thus, variations in heating known in the art, such as holding at one temperature for a certain period of time and then raising the temperature to a second temperature over the course of a second period of time, are contemplated by the present disclosure. Furthermore, heating may be carried out in any suitable atmosphere, such as air, or other oxidizing gas, reducing gas, inert gas or mixtures thereof. The equipment used for such heating may use a static or flowing atmosphere of such gases to effect reduction, preferably a flowing atmosphere.

Optionally, the impregnated carrier may be dried in the presence of an atmosphere which reduces the silver compound to metallic silver. Drying methods known in the art include steam drying, drying in an atmosphere with a controlled oxygen concentration, drying in a reducing atmosphere, and air drying.

After reduction, suitable silver particle sizes may be in the range of from 1 to 1000 nm in diameter, or from greater than 10 to less than 500 nm in diameter. Although not necessary, it is generally preferred for the silver to be relatively uniformly deposited on the fluoride-mineralized alpha-alumina carrier.

Having generally described the invention, a further understanding may be obtained by reference to the following examples, which are provided for purposes of illustration only and are not intended to be limiting unless otherwise specified.

The method of the invention will now be illustrated by the following non-limiting examples.

EXAMPLES

Example 1—Preparation of Conventional Catalysts A, B, C

Three separate catalyst compositions A, B, and C comprising silver, rhenium promoter and alkali metal promoters on different conventional (non-fluoride mineralized) alpha-alumina carriers A and B. As shown in Table 1 below, catalyst A was prepared on carrier A, while catalysts B and C were prepared on carrier B.

All catalysts were prepared in accordance with known methods, for example as described in WO 2006/133183 A2. Carriers A and B each had a surface area in the range of 0.7 to 3.0 m²/g, as measured in accordance with the B.E.T. method.

Catalysts A, B, and C each comprised silver, rhenium, tungsten, sulfur, lithium, potassium and cesium.

Example 2—Preparation of EMA Catalysts D to K

As shown in Table 1 below, various catalyst compositions D to K comprising silver, rhenium promoter and alkali metal promoters on different fluoride-mineralized alpha-alumina (FMA) carriers C to G were prepared in accordance with known methods, for example as described in WO 2006/133183 A2.

The fluoride-mineralized alpha-alumina carriers C to G used in said catalyst compositions each had a lamellar or platelet-type morphology such that particles having in at least one direction a size greater than 0.1 micrometer had at least one substantially flat major surface. Furthermore, said fluoride-mineralized alpha-alumina carriers each had a surface area in the range of 0.7 to 3.0 m²/g, as measured in accordance with the B.E.T. method. Said fluoride-mineralized alpha-alumina carriers were each made in accordance with known methods described in US 2018/0161761 A1 from a mixture comprising alpha-alumina precursors, a fluoride-mineralizing agent and water.

Catalysts D through K each comprised silver, rhenium, tungsten, sulfur, lithium, potassium and cesium.

TABLE 1

Catalysts and Corresponding Carriers

| Catalyst Example | Carrier Employed |
|---|---|
| A | A |
| B | B |
| C | B |
| D | C |
| E | C |
| F | D |
| G | E |
| H | E |
| I | E |

40

TABLE 1-continued

Catalysts and Corresponding Carriers

| Catalyst Example | Carrier Employed |
|---|---|
| J | E |
| K | G |

Example 3—Testing of Catalysts A to G and K at Condition 1

Catalysts A to G and catalyst K described above were each tested according to the following method found in Example 3 of U.S. Pat. No. 8,084,390 B2.

Each catalyst was used to produce ethylene oxide from ethylene and oxygen.

To do this, crushed catalyst was loaded into a stainless steel U-shaped tube. The tube was immersed in a molten metal bath (heat medium) and the ends were connected to a gas flow system. The weight of catalyst used and the inlet gas flow rate (0.249 Nl/minute) were adjusted to give a gas hourly space velocity of 3300 Nl/(1·h), as calculated for uncrushed catalyst. The inlet gas pressure was 1550 kPa (absolute).

The gas mixture passed through the catalyst bed, in a "once-through" operation, during the entire test run including the start-up, consisted of 30.0 volume percent ethylene, 8.0 volume percent oxygen, 5.0 volume percent carbon dioxide, 57 volume percent nitrogen, and 1.0 to 6.0 parts per million by volume (ppmv) ethyl chloride.

The initial reactor temperature was 180° C., and this was ramped up at a rate of 10° C. per hour to 225° C. and then adjusted so as to achieve a constant ethylene oxide content of 3.1 volume percent in the outlet gas stream at an ethyl chloride concentration of 2.0 ppmv.

Performance data at this conversion level are usually obtained for initial peak selectivity. Depending upon the catalyst used and the parameters of the ethylene epoxidation process, the time required to reach the initial, peak selectivity, that is the highest selectivity reached in the initial stage of the process, may vary. Over the course of the entire testing run, the reactor temperature was adjusted to maintain an outlet EO concentration of 3.1 vol %, corresponding to a production work rate of 200 kg EO/m³ catalyst per hour. The ethyl chloride concentration was periodically adjusted to maintain maximum catalyst selectivity.

Example 4—Testing of Catalysts A, B, E, H, I at Condition 2

Each of Catalysts A, B, E, H, and I were also tested according to the following method.

Each catalyst was used to produce ethylene oxide from ethylene and oxygen.

To do this, crushed catalyst was loaded into a stainless steel U-shaped tube. The tube was immersed in a molten metal bath (heat medium) and the ends were connected to a gas flow system. The weight of catalyst used and the inlet gas flow rate (0.249 Nl/minute) were adjusted to give a gas hourly space velocity of 4800 Nl/(1·h), as calculated for uncrushed catalyst. The inlet gas pressure was 2000 kPa (absolute).

The gas mixture passed through the catalyst bed, in a "once-through" operation, during the entire test run including the start-up, consisted of 35.0 volume percent ethylene, 7.3 volume percent oxygen, 0.7 volume percent carbon dioxide, 57 volume percent nitrogen, and 0.8 to 6.5 parts per million by volume (ppmv) ethyl chloride.

The initial reactor temperature was 180° C., and this was ramped up at a rate of 10° C. per hour to 225° C. and then adjusted so as to achieve a constant ethylene oxide content of 3.0 volume percent in the outlet gas stream at an ethyl chloride concentration of 1.8 ppmv.

Performance data at this conversion level are usually obtained for initial peak selectivity. Depending upon the catalyst used and the parameters of the ethylene epoxidation process, the time required to reach the initial, peak selectivity, that is the highest selectivity reached in the initial stage of the process, may vary. Over the course of the entire testing run the reactor temperature was adjusted to maintain an outlet EO concentration of 3.0 vol %, corresponding to a production work rate of 280 kg EO/m³ catalyst per hour. The ethyl chloride concentration was periodically adjusted to maintain maximum catalyst selectivity.

A comparison of reactor test conditions described in Examples 3 and 4 above is shown in Table 2 below.

TABLE 2

| Catalyst Testing Conditions | | |
| --- | --- | --- |
| Test Condition | Condition 1 | Condition 2 |
| GHSV, Nl/ (1 · h) | 3300 | 4800 |
| Inlet pressure kPa absolute | 1550 | 2000 |
| Feed Ethylene, % m | 30 | 35 |
| Feed Oxygen, % m | 8.0 | 7.3 |
| Feed CO₂, % m | 5.0 | 0.7 |
| Outlet EO, % m | 3.1 | 3.0 |
| Work rate, kg/m³/hr | 200 | 280 |
| Ethyl Chloride (EC) Reaction modifier, ppm | 1.0 to 6.0 | 0.8 to 6.5 |

Example 5—Catalyst Testing Results at Condition 1

The testing results for Catalysts A through G and catalyst K at Condition 1 are shown graphically in FIGS. 2 to 4.

FIG. 2 shows the activity profiles for conventional Catalysts A, B and C and also FMA Catalysts D, E, F, G, and K tested at Condition 1 and a constant outlet EO concentration of 3.1 vol % over a cumulative EO production period varying from 1.6 to 3.0 kton EO/m³ catalyst.

FIG. 3 shows the optimum overall chloriding effectiveness values ($Cl_{eff}$) for Catalysts A to G and catalyst K over that same production period. From this figure, it is clear that the optimum overall chloriding effectiveness values for Catalysts D through G and K remain stable, while they nearly double over time for Catalysts A, B and C.

All Catalysts A through G and K have achieved stable, steady-state operation by 0.2 kton/m³ of cumulative ethylene oxide production. At 0.2 kton/m³ of cumulative ethylene oxide production, the optimum overall chloriding effectiveness values for Catalysts A, B, C, D, E, F, G and K are 12.0, 8.0, 12.3, 9.1, 7.2, 7.4, 8.1, and 6.3 respectively. These values were used to calculate the ratio of the optimum overall chloriding effectiveness value at any time ($Cl_{eff_x}$) to the optimum overall chloriding effectiveness value at 0.2 kton/m³ cumulative ethylene oxide production ($Cl_{eff_1}$). The results of this calculation are shown in FIG. 4. The values of this ratio for Catalysts A, B and C soon exceed 1.2 and continuously rise during the entire catalyst run. Surprisingly, this ratio remains between 0.8 and 1.2 for the entire runs of Catalysts D, E, F, G, and K beyond 0.2 kton/m³ cumulative ethylene oxide production.

Example 6—Catalyst Testing Results at Condition 2

The testing results for Catalysts A, B, E, H, and I at Condition 2 are shown graphically in FIGS. 5 to 7.

FIG. 5 shows the activity profiles for conventional Catalysts A and B and also EMA Catalysts E, H, and I tested at Condition 2 and a constant outlet EO concentration of 3.0 vol % over a cumulative EO production period varying from 2.1 to 4.5 kton EO/m³ catalyst.

FIG. 6 shows the optimum overall chloriding effectiveness values ($Cl_{eff}$) for Catalysts A, B, E, H, and I over that same production period. From this figure, it is clear that the optimum overall chloriding effectiveness values for Catalyst E, H, and I remain stable, while they nearly double over time for Catalysts A and B.

All Catalysts A, B, E, H and I have achieved stable, steady-state operation by 0.2 kton/m³ of cumulative ethylene oxide production. At 0.2 kton/m³ of cumulative ethylene oxide production, the optimum overall chloriding effectiveness values for Catalysts A, B, E, H, and I are 12.6, 5.7, 6.0, 6.0, and 5.7. These values were used to calculate the ratio of the optimum overall chloriding effectiveness value at any time ($Cl_{eff_x}$) to the optimum overall chloriding effectiveness value at 0.2 kton/m³ cumulative ethylene oxide production ($Cl_{eff_1}$). The results of this calculation are shown in FIG. 7. The values of this ratio for Catalysts A and B soon exceed 1.2 and continuously rise during the entire catalyst run. Surprisingly, this ratio remains between 0.8 and 1.2 for the entire runs of Catalysts E, H, and I beyond 0.2 kton/m³ cumulative ethylene oxide production. Indeed, this ratio even remains between 0.9 and 1.1 for the entire run of Catalysts E and I.

Example 7—Repeat Catalyst Testing Results at Condition 1

Catalyst J was tested two different times at Condition 1 and a constant outlet EO concentration of 3.1 vol % over a cumulative EO production period ranging from 1.5 to 1.9 kton EO/m³ catalyst.

The purpose of these repeat tests was to demonstrate the reproducibility of the stability of the chloriding effectiveness value over multiple runs of the same catalyst formulation. Although the initial optimum overall chloriding effectiveness value differed slightly between the runs due to normal laboratory operating and measurement variations, each run demonstrated remarkable stability of the chloriding effective value over time.

In the repeat runs of Catalyst J, the optimum overall chloriding effectiveness values at a cumulative ethylene oxide production of 0.2 kton/m³ were 6.7, and 7.0. These values were used to calculate the ratio of the optimal overall chloriding effectiveness value at any time ($Cl_{eff_x}$) to the optimal overall chloriding effectiveness value at 0.2 kton/m³ cumulative ethylene oxide production ($Cl_{eff_1}$) for each corresponding run and compared with the test results of Catalysts A and B at Condition 1 (previously discussed).

The results of these two repeat runs of Catalyst J at Condition 1 are shown in FIG. 8. As previously shown, the values of the overall chloriding effectiveness ratio for Catalysts A and B soon exceed 1.2 and continuously rise during the entire catalyst run. However, this ratio remains between 0.8 and 1.2 for both repeat runs of Catalyst J beyond 0.2 kton/m$^3$ cumulative ethylene oxide production. Indeed, this ratio even remains between 0.9 and 1.1 for nearly the entire run 1 of Catalyst J.

In order to address the possible effect of dopant variability on the $Cl_{eff}$ requirement, a comparison of catalysts with similar dopant levels but on different carriers was made. A selection of the relative dopant levels for catalysts C, D, and E are given in Table 3. Here, dopant levels are calculated as a ratio relative to the comparative catalyst C. It is apparent from Table 3 that these catalysts contained only minor differences in the relative amounts of dopants and thus provide a means to remove the variable of differences in dopant levels influencing the moderator concentration requirement. This also provides an additional means to compare the FMA and non-EMA carrier effects on the catalyst performance as it relates to the chloride moderator requirements during operation.

The data in Table 3 shows that catalysts C, D, and E have very similar dopant formulations. Despite this similarity, there is a dramatically different behavior when comparing the reaction modifier concentration requirements of catalyst C with those of catalysts D and E.

The converse is also true, since wide dopant ranges for both carrier types are represented in catalysts A, B, and C for the non-FMA catalysts, and also in catalysts D through K for FMA catalysts. Yet the significant increase in the $Cl_{eff}$ requirement is seen only in the comparative non-FMA carrier based catalysts.

TABLE 3

Relative Dopant Levels for Selected Catalysts

| Catalyst | Re | W | S | Li | K | Cs |
|---|---|---|---|---|---|---|
| C * | 1.0 | 1.0 | 1.0 | 1.0 | 1.0 | 1.0 |
| D ** | 1.1 | 1.0 | 1.0 | 1.0 | 1.0 | 0.9 |
| E ** | 1.1 | 1.0 | 1.0 | 1.0 | 1.0 | 1.1 |

* Comparative
** According to the Invention

CONCLUSIONS

The lifetime of a typical commercial ethylene oxide catalyst is dependent upon many factors, including catalyst type, operating conditions, equipment and feed constraints, operator economics, statutory inspection requirements, catalyst poisoning events, etc. However, a typical range of catalyst life in terms of cumulative ethylene oxide production is from 1.5 to over 4.0 kton EO/m$^3$. That is to say, the data presented herein in the Examples is representative of commercial performance.

Conventional (non-FMA carrier based) catalysts A, B and C displayed a typical reaction modifier concentration profile over catalyst life. As previously described in the prior art, as the catalyst temperature increased due to long term deactivation, the optimum reaction modifier concentration (i.e., optimum overall chloriding effectiveness value) required an increase in order to maintain maximum catalyst selectivity. For catalysts A, B and C, the reaction modifier concentration (as described by $Cl_{eff}$) nearly doubled over the course of catalyst operation at both Conditions 1 and 2.

Surprisingly, catalysts D to K on FMA carriers displayed a very different reaction modifier profile over catalyst life. Each of these catalysts displayed remarkable stability of the reaction modifier concentration over the entire catalyst life, as indicated by ratio of $Cl_{eff}$ at any point x ($Cl_{effx}$) to the $Cl_{eff}$ at 0.2 kton/m$^3$ cumulative ethylene oxide production ($Cl_{eff1}$) remaining within the narrow range of 0.8 to 1.2. This effect is independent of the operating conditions chosen, as catalyst E demonstrated this technical effect at both Conditions 1 and 2. This effect is also independent of the catalyst dopant formulation, as evidenced by the differences in behavior between catalyst C and catalysts D and E. Within each carrier type, the wide range of dopant levels has no impact on the behavior of the catalysts in terms of moderator level demand. That is to say, variations in dopant levels for catalysts A, B, and C all produce the requirement for an increase in chloride moderator over the catalyst lifetime. In contrast to the non-FMA catalysts, the FMA catalysts D through K with a wide range of dopant levels all show only a small variation in moderator requirement over the life of the catalyst.

Practically speaking, this means that the commercial plant operator has an advantage in operating according to the claims of the present invention. In the past, the operator would continuously have to adjust the reaction modifier concentration (i.e., the overall chloriding effectiveness value) in order to maintain an optimum level that is constantly changing with time. This trial-and-error process of seeking a moving optimum opens up the plant operator to attain sub-optimal selectivity performance if the chosen $Cl_{eff}$ is either too high (over-moderated) or too low (under-moderated). However, according to the present invention and as demonstrated in the Examples, the same plant operator can confidently maintain the reaction modifier concentration (i.e., $Cl_{eff}$) at a constant or near constant value throughout the entire catalyst life to ensure maximum catalyst performance.

We claim:

1. A process for the epoxidation of ethylene comprising:
contacting an inlet feed gas comprising ethylene, oxygen and one or more reaction modifiers consisting of organic chlorides with an epoxidation catalyst comprising a carrier, and having silver, a rhenium promoter, and one or more alkali metal promoters deposited thereon;
wherein the inlet feed gas has an overall catalyst chloriding effectiveness value ($Cl_{eff}$) represented by the formula:—

$$Cl_{eff} = \frac{(0.1 * [MC] + [EC] + 2 * [EDC] + [VC])}{(0.002 * [CH_4] + [C_2H_6] + 0.01 * [C_2H_4])} \quad (I)$$

wherein [MC], [EC], [EDC], and [VC] are the concentrations in ppmv of methyl chloride (MC), ethyl chloride (EC), ethylene dichloride (EDC), and vinyl chloride (VC), respectively, and [CH$_4$], [C$_2$H$_6$] and [C$_2$H$_4$] are the concentrations in mole percent of methane, ethane, and ethylene, respectively, in the inlet feed gas;
wherein at an initial cumulative ethylene oxide production cumEO$_1$ of at least 0.2 kton ethylene oxide/m$^3$ catalyst, said process is operating at a reaction temperature having a value T$_1$ and with the inlet feed gas having an optimum overall catalyst chloriding effectiveness value of $Cl_{eff1}$ to produce ethylene oxide with an ethylene oxide production parameter at a target value EO$_1$; and characterised in that the carrier is a fluoride-mineralized alpha-alumina carrier and said process is subsequently operated such that at a cumulative ethylene oxide production cumEO$_x$, wherein cumEO$_x$ is at least 0.6 kton ethylene oxide/m$^3$ catalyst greater than cumEO$_1$, the reaction temperature has an increased value T$_x$ to maintain said ethylene oxide production parameter at the target value EO$_1$ whilst the optimum overall catalyst chloriding effectiveness value of the inlet feed gas Cl$_{effx}$ is controlled such that the ratio of Cl$_{effx}$/Cl$_{eff1}$ is in the range of from 0.8 to 1.2, wherein the value T1 is the reaction temperature when the ethylene oxide production is at cumEO1, and wherein the value Tx is greater than the value T1 by at least 3° C.

2. The process of claim 1, wherein cumEO$_1$ is at least 0.25 kton ethylene oxide/m$^3$ catalyst.

3. The process of claim 1, wherein cumEO$_x$ is at least 0.8 kton ethylene oxide/m$^3$ catalyst greater than cumEO$_1$.

4. The process of claim 1, wherein the ratio of Cl$_{effx}$/Cl$_{eff1}$ is in the range of from 0.9 to 1.1.

5. The process of claim 1, wherein as cumulative ethylene oxide production increases from cumEO$_1$ to cumEO$_x$, the ratio of Cl$_{effx}$/Cl$_{eff1}$ is maintained throughout the period of said increase in the range of from 0.8 to 1.2.

6. The process of claim 1, wherein as cumulative ethylene oxide production increases from cumEO$_1$ to reach its final value of cumEO$_x$ at the end of catalyst life, the ratio of Cl$_{effx}$/Cl$_{eff1}$ is maintained throughout the entire life of the catalyst in the range of from 0.8 to 1.2.

7. The process of claim 1, wherein the reaction temperature T$_1$ is at a value in the range of from 180 to 260° C.

8. The process of claim 1, wherein the reaction temperature T$_x$ is at a value in the range of from 200 to 300° C.

9. The process of claim 1, wherein the ethylene oxide production parameter, EO$_1$, is work rate and EO$_1$ is selected from in the range of from 50 to 600 kg of ethylene oxide per m$^3$ of catalyst per hour.

10. The process of claim 1, wherein the inlet feed gas further comprises carbon dioxide in a concentration of from 0.10 mole-% to 10 mole-%, relative to the total inlet feed gas.

11. The process of claim 1, wherein one or more reaction modifiers are selected from methyl chloride, ethyl chloride, ethylene dichloride, vinyl chloride, and combinations thereof.

12. The process of claim 1, wherein the one or more alkali metal promoters are selected from the group consisting of lithium, sodium, potassium, rubidium, cesium, and a combination thereof.

13. The process of claim 1, wherein the epoxidation catalyst further comprises one or more co-promoters selected from the group consisting of sulfur, phosphorus, boron, tungsten, molybdenum, chromium, and a combination thereof.

14. The process of claim 1, wherein the epoxidation catalyst comprises:

a first co-promoter selected from the group consisting of sulfur, phosphorus, boron, and a combination thereof; and a second co-promoter selected from the group consisting of tungsten, molybdenum, chromium, and a combination thereof.

15. The process of claim 1, wherein the epoxidation catalyst further comprises a further metal selected from the group consisting of beryllium, magnesium, calcium, strontium, barium, titanium, hafnium, zirconium, vanadium, thallium, thorium, tantalum, niobium, gallium, germanium, manganese, and a combination thereof.

16. The process of claim 1, wherein the fluoride-mineralized alpha-alumina carrier has a surface area in the range of from 0.1 to 10 m$^2$/g relative to the weight of the fluoride-mineralized alpha-alumina carrier, as measured in accordance with the B.E.T. method.

17. The process of claim 1, wherein the fluoride-mineralized alpha-alumina carrier has a particulate matrix having a lamellar or platelet-type morphology.

18. The process as claimed in claim 17, wherein the lamellar or platelet-type morphology is such that particles having in at least one direction a size greater than 0.1 micrometer have at least one substantially flat major surface.

19. The process of claim 1, further comprising:

reacting at least a portion of the ethylene oxide produced with at least one reagent selected from the group consisting of: water, an alcohol, carbon dioxide and an amine to form ethylene glycol, an ethylene glycol ether, ethylene carbonate and ethanolamine, respectively.

* * * * *